Figure 1:
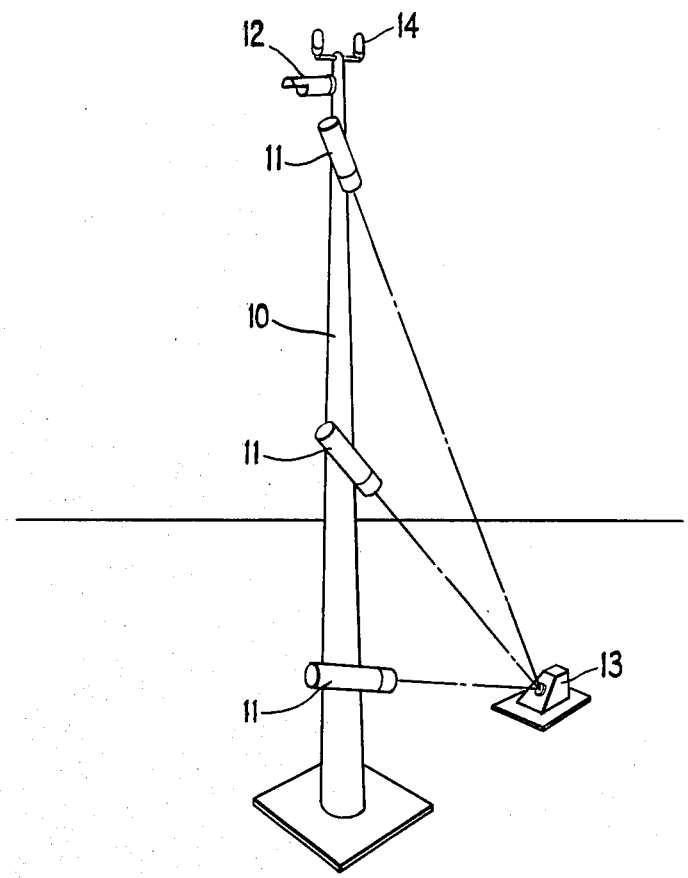

United States Patent [19]

Puffett

[11] 4,419,731

[45] Dec. 6, 1983

[54] APPARATUS FOR ESTIMATING SLANT VISIBILITY IN FOG

[75] Inventor: Alan W. Puffett, Bedford, England

[73] Assignee: The Secretary of State for Defence in Her Britannic Majesty's Government of the United Kingdom of Great Britain and Northern Ireland, London, England

[21] Appl. No.: 224,563

[22] PCT Filed: Mar. 18, 1980

[86] PCT No.: PCT/GB80/00046

§ 371 Date: Nov. 17, 1980

§ 102(e) Date: Nov. 17, 1980

[87] PCT Pub. No.: WO80/02073

PCT Pub. Date: Oct. 2, 1980

[30] Foreign Application Priority Data

Mar. 19, 1979 [GB] United Kingdom ............... 7909508

[51] Int. Cl.³ .................... G01C 3/08; G06F 15/48
[52] U.S. Cl. ........................... 364/428; 343/5 W; 356/4; 364/433
[58] Field of Search .................. 364/428–430, 364/433, 435, 578; 73/170 R; 343/5 W; 356/4

[56] References Cited

U.S. PATENT DOCUMENTS 3,650,627 3/1972 Noxon ............................ 343/5 W
3,702,565 11/1972 Moses et al. .

OTHER PUBLICATIONS

"Opto-Electronics Signal Processing Techniques" Lasers for Measuring Slant Visual Range by E. T. Hill, pp. 35-35-9.

Primary Examiner—Errol A. Krass
Attorney, Agent, or Firm—Cushman, Darby & Cushman

[57] ABSTRACT

Apparatus for estimating the slant visibility in obscured atmospheres such as fog, whereby an indication is derived as to when, during an aircraft landing approach in such conditions, the aircrew are likely to be able to see the runway lights. The apparatus comprises a transmissometer array arranged to take visibility readings over a slanted distance from different heights not far from a runway threshold, and a computer arranged to compare the readings with a plurality of fog profile models, to determine the definitive model and hence to derive and indicate a visual acquisition estimate.

17 Claims, 15 Drawing Figures

FIG. 7a

| HGT | DIST | POSN | RANGE | LAT | ELEV | AZ | ANGLE | EFF INT | P/C I | KM*-1 | BLOCKS TYPE | E L E V | A Z N | I N T | ELEMENTS L A M P | L F O G | H G T | L A T | T E S T | |
|---|---|---|---|---|---|---|---|---|---|---|---|---|---|---|---|---|---|---|---|---|
| 8.900 | -400.1 | -1020.1 | -620 | -0.0 | -1.73 | -0.00 | 1.73 | 1366.4 | 18.2 | 11.094 | 2 | 5 | 1 | 2 | 2 | 1 | 1 | 1 | 0 | 26 |
| 8.900 | -400.2 | -1010.2 | -610 | -0.0 | -1.73 | -0.00 | 1.73 | 1366.0 | 18.2 | 11.094 | 2 | 5 | 1 | 2 | 2 | 1 | 2 | 1 | 0 | 19 |
| 8.990 | -400.1 | -1000.1 | -600 | -0.0 | -1.71 | -0.00 | 1.71 | 1376.3 | 18.4 | 11.117 | 2 | 5 | 1 | 2 | 2 | 1 | 2 | 1 | 0 | 19 |
| 9.171 | -399.9 | -989.9 | -590 | -0.0 | -1.69 | -0.00 | 1.69 | 1396.6 | 18.6 | 11.160 | 2 | 5 | 1 | 2 | 2 | 1 | 2 | 1 | 0 | 19 |
| 9.352 | -399.8 | -979.8 | -580 | -0.0 | -1.66 | -0.00 | 1.66 | 1416.9 | 18.9 | 11.203 | 2 | 5 | 1 | 2 | 2 | 1 | 2 | 1 | 0 | 19 |
| 9.533 | -399.6 | -969.6 | -570 | -0.0 | -1.63 | -0.00 | 1.63 | 1437.2 | 19.2 | 11.246 | 2 | 5 | 1 | 2 | 2 | 1 | 2 | 1 | 0 | 19 |
| 9.714 | -399.5 | -959.5 | -560 | -0.0 | -1.61 | -0.00 | 1.61 | 1457.5 | 19.4 | 11.288 | 2 | 5 | 1 | 2 | 2 | 1 | 2 | 1 | 0 | 20 |
| 9.894 | -399.0 | -949.0 | -550 | -0.0 | -1.58 | -0.00 | 1.58 | 1478.7 | 19.7 | 11.330 | 2 | 5 | 1 | 2 | 2 | 1 | 2 | 1 | 0 | 19 |
| 10.08 | -398.9 | -938.9 | -540 | -0.0 | -1.55 | -0.00 | 1.55 | 1499.1 | 20.0 | 11.371 | 2 | 5 | 1 | 2 | 2 | 1 | 2 | 1 | 0 | 19 |
| 10.26 | -398.8 | -928.8 | -530 | -0.0 | -1.53 | -0.00 | 1.53 | 1519.5 | 20.3 | 11.411 | 2 | 5 | 1 | 2 | 2 | 1 | 2 | 1 | 0 | 19 |
| 10.44 | -398.6 | -918.6 | -520 | -0.0 | -1.50 | -0.00 | 1.50 | 1539.9 | 20.5 | 11.452 | 2 | 5 | 1 | 2 | 2 | 1 | 2 | 1 | 0 | 19 |
| 10.62 | -398.5 | -908.5 | -510 | -0.0 | -1.47 | -0.00 | 1.47 | 1560.3 | 20.8 | 11.491 | 2 | 5 | 1 | 2 | 2 | 1 | 2 | 1 | 0 | 19 |
| 10.80 | -398.3 | -898.3 | -500 | -0.0 | -1.45 | -0.00 | 1.45 | 1580.8 | 21.1 | 11.530 | 2 | 5 | 1 | 2 | 2 | 1 | 2 | 1 | 0 | 19 |
| 10.98 | -398.2 | -888.2 | -490 | -0.0 | -1.42 | -0.00 | 1.42 | 1601.2 | 21.3 | 11.569 | 2 | 5 | 1 | 2 | 2 | 1 | 2 | 1 | 0 | 19 |
| 11.16 | -398.0 | -878.0 | -480 | -0.0 | -1.39 | -0.00 | 1.39 | 1621.7 | 21.6 | 11.608 | 2 | 5 | 1 | 2 | 2 | 1 | 2 | 1 | 0 | 19 |
| 11.34 | -397.9 | -867.9 | -470 | -0.0 | -1.37 | -0.00 | 1.37 | 1642.1 | 21.9 | 11.646 | 2 | 5 | 1 | 2 | 2 | 1 | 2 | 1 | 0 | 19 |
| 11.52 | -397.8 | -857.8 | -460 | -0.0 | -1.34 | -0.00 | 1.34 | 1662.6 | 22.2 | 11.683 | 2 | 5 | 1 | 2 | 2 | 1 | 2 | 1 | 0 | 19 |
| 11.70 | -397.6 | -847.6 | -450 | -0.0 | -1.31 | -0.00 | 1.31 | 1683.1 | 22.4 | 11.720 | 2 | 5 | 1 | 2 | 2 | 1 | 2 | 1 | 0 | 19 |
| 11.88 | -397.5 | -837.5 | -440 | -0.0 | -1.29 | -0.00 | 1.29 | 1703.7 | 22.7 | 11.757 | 2 | 5 | 1 | 2 | 2 | 1 | 2 | 1 | 0 | 19 |
| 12.06 | -397.3 | -827.3 | -430 | -0.0 | -1.26 | -0.00 | 1.26 | 1724.2 | 23.0 | 11.794 | 2 | 5 | 1 | 2 | 2 | 1 | 2 | 1 | 0 | 19 |
| 12.24 | -397.2 | -817.2 | -420 | -0.0 | -1.23 | -0.00 | 1.23 | 1744.7 | 23.3 | 11.830 | 2 | 5 | 1 | 2 | 2 | 1 | 2 | 1 | 0 | 19 |
| 12.43 | -397.0 | -807.0 | -410 | -0.0 | -1.21 | -0.00 | 1.21 | 1765.3 | 23.5 | 11.866 | 2 | 5 | 1 | 2 | 2 | 1 | 2 | 1 | 0 | 19 |
| 12.61 | -396.9 | -796.9 | -400 | -0.0 | -1.18 | -0.00 | 1.18 | 1785.9 | 23.8 | 11.901 | 2 | 5 | 1 | 2 | 2 | 1 | 2 | 1 | 0 | 19 |
| 12.79 | -396.7 | -786.7 | -390 | -0.0 | -1.15 | -0.00 | 1.15 | 1806.5 | 24.1 | 11.936 | 2 | 5 | 1 | 2 | 2 | 1 | 2 | 1 | 0 | 19 |
| 12.97 | -396.6 | -776.6 | -380 | -0.0 | -1.13 | -0.00 | 1.13 | 1827.1 | 24.4 | 11.971 | 2 | 5 | 1 | 2 | 2 | 1 | 2 | 1 | 0 | 19 |
| 13.15 | -396.5 | -766.5 | -370 | -0.0 | -1.10 | -0.00 | 1.10 | 1847.7 | 24.6 | 12.005 | 2 | 5 | 1 | 2 | 2 | 1 | 2 | 1 | 0 | 19 |
| 13.33 | -396.3 | -756.3 | -360 | -0.0 | -1.07 | -0.00 | 1.07 | 1868.3 | 24.9 | 12.039 | 2 | 5 | 1 | 2 | 2 | 1 | 2 | 1 | 0 | 19 |
| 13.51 | -396.2 | -746.2 | -350 | -0.0 | -1.05 | -0.00 | 1.05 | 1889.0 | 25.2 | 12.073 | 2 | 5 | 1 | 2 | 2 | 1 | 2 | 1 | 0 | 19 |

FIG. 7b

| HGT | DIST | POSN | RANGE | LAT | ELEV | AZ | ANGLE | EFF INT | P/C I | KM*-1 | BLOCKS TYPE | EV | AN | INT | ELEMENTS LATP | FOG | HGT | LAT | TEST |
|---|---|---|---|---|---|---|---|---|---|---|---|---|---|---|---|---|---|---|---|
| 13.71 | -396.0 | -736.0 | -340 | -0.0 | -1.02 | -0.00 | 1.02 | 1912.1 | 25.5 | 12.111 | 2 | 5 | 1 | 2 | 2 | 1 | 3 | 1 | 0 |
| 13.94 | -395.6 | -725.6 | -330 | -0.0 | -0.98 | -0.00 | 0.98 | 1939.1 | 25.9 | 12.153 | 2 | 5 | 1 | 2 | 2 | 1 | 3 | 1 | 0 |
| 14.17 | -395.4 | -715.4 | -320 | -0.0 | -0.95 | -0.00 | 0.95 | 1964.8 | 26.2 | 12.194 | 2 | 5 | 1 | 2 | 2 | 1 | 3 | 1 | 0 |
| 14.39 | -395.3 | -705.3 | -310 | -0.0 | -0.91 | -0.00 | 0.91 | 1990.6 | 26.5 | 12.234 | 2 | 5 | 1 | 2 | 2 | 1 | 3 | 1 | 0 |
| 14.62 | -395.1 | -695.1 | -300 | -0.0 | -0.88 | -0.00 | 0.88 | 2016.5 | 26.9 | 12.275 | 2 | 5 | 1 | 2 | 2 | 1 | 3 | 1 | 0 |
| 14.84 | -395.0 | -685.0 | -290 | -0.0 | -0.85 | -0.00 | 0.85 | 2042.3 | 27.2 | 12.315 | 2 | 5 | 1 | 2 | 2 | 1 | 3 | 1 | 0 |
| 15.07 | -394.9 | -674.9 | -280 | -0.0 | -0.81 | -0.00 | 0.81 | 2068.1 | 27.6 | 12.354 | 2 | 5 | 1 | 2 | 2 | 1 | 3 | 1 | 0 |
| 15.30 | -394.7 | -664.7 | -270 | -0.0 | -0.78 | -0.00 | 0.78 | 2094.0 | 27.9 | 12.394 | 2 | 5 | 1 | 2 | 2 | 1 | 3 | 1 | 0 |
| 15.52 | -394.6 | -654.6 | -260 | -0.0 | -0.75 | -0.00 | 0.75 | 2119.9 | 28.3 | 12.432 | 2 | 5 | 1 | 2 | 2 | 1 | 3 | 1 | 0 |
| 15.75 | -394.1 | -644.1 | -250 | -0.0 | -0.71 | -0.00 | 0.71 | 2147.2 | 28.6 | 12.471 | 2 | 5 | 1 | 2 | 2 | 1 | 3 | 1 | 0 |
| 15.98 | -394.0 | -634.0 | -240 | -0.0 | -0.68 | -0.00 | 0.68 | 2173.1 | 29.0 | 12.509 | 2 | 5 | 1 | 2 | 2 | 1 | 3 | 1 | 0 |
| 16.20 | -393.7 | -623.8 | -230 | -0.0 | -0.64 | -0.00 | 0.64 | 2199.1 | 29.3 | 12.547 | 2 | 5 | 1 | 2 | 2 | 1 | 3 | 1 | 0 |
| 16.43 | -393.7 | -613.7 | -220 | -0.0 | -0.61 | -0.00 | 0.61 | 2225.1 | 29.7 | 12.584 | 2 | 5 | 1 | 2 | 2 | 1 | 3 | 1 | 0 |
| 16.66 | -393.5 | -603.5 | -210 | -0.0 | -0.58 | -0.00 | 0.58 | 2251.1 | 30.0 | 12.621 | 2 | 5 | 1 | 2 | 2 | 1 | 3 | 1 | 0 |
| 16.88 | -393.4 | -593.4 | -200 | -0.0 | -0.54 | -0.00 | 0.54 | 2277.1 | 30.4 | 12.658 | 2 | 5 | 1 | 2 | 2 | 1 | 3 | 1 | 0 |
| 17.11 | -393.2 | -583.2 | -190 | -0.0 | -0.51 | -0.00 | 0.51 | 2303.1 | 30.7 | 12.695 | 2 | 5 | 1 | 2 | 2 | 1 | 3 | 1 | 0 |
| 17.33 | -392.8 | -572.8 | -180 | -0.0 | -0.47 | -0.00 | 0.47 | 2318.9 | 30.9 | 12.731 | 2 | 5 | 1 | 2 | 2 | 1 | 3 | 1 | 0 |
| 17.56 | -392.3 | -562.3 | -170 | -0.0 | -0.44 | -0.00 | 0.44 | 2330.7 | 31.1 | 12.767 | 2 | 5 | 1 | 2 | 2 | 1 | 3 | 1 | 0 |
| 17.79 | -391.9 | -551.9 | -160 | -0.0 | -0.40 | -0.00 | 0.40 | 2342.6 | 31.2 | 12.802 | 2 | 5 | 1 | 2 | 2 | 1 | 3 | 1 | 0 |

FIG. 7c

| HGT | DIST | POSN | RANGE LAT | ELEV | AZ | ANGLE | EFF INT | P/C I | KM*-1 | BLOCKS T Y P E | E L E V | A N T | ELEMENTS L A M P | F O G | H I G T | L A T | T E S T | | | | |
|---|---|---|---|---|---|---|---|---|---|---|---|---|---|---|---|---|---|---|---|---|---|
| 18.05 | -391.1 | -541.1 | -150 | -0.0 | -0.36 | -0.00 | 0.36 | 2357.1 | 31.4 | 12.844 | 2 | 5 | 1 | 2 | 1 | 1 | 4 | 1 | 0 | 20 |
| 18.36 | -390.7 | -530.7 | -140 | -0.0 | -0.31 | -0.00 | 0.31 | 2372.9 | 31.6 | 12.891 | 2 | 5 | 1 | 2 | 1 | 1 | 4 | 1 | 0 | 20 |
| 18.66 | -389.9 | -519.9 | -130 | -0.0 | -0.26 | -0.00 | 0.26 | 2389.4 | 31.9 | 12.938 | 2 | 5 | 1 | 2 | 1 | 1 | 4 | 1 | 0 | 20 |
| 18.97 | -389.1 | -509.1 | -120 | -0.0 | -0.21 | -0.00 | 0.21 | 2406.0 | 32.1 | 12.984 | 2 | 5 | 1 | 2 | 1 | 1 | 4 | 1 | 0 | 20 |
| 19.27 | -388.7 | -498.7 | -110 | -0.0 | -0.16 | -0.00 | 0.16 | 2421.9 | 32.3 | 13.030 | 2 | 5 | 1 | 2 | 1 | 1 | 4 | 1 | 0 | 20 |
| 19.58 | -387.4 | -487.4 | -100 | -0.0 | -0.11 | -0.00 | 0.11 | 2438.6 | 32.5 | 13.075 | 2 | 5 | 1 | 2 | 1 | 1 | 4 | 1 | 0 | 20 |
| 19.88 | -387.0 | -477.0 | -90 | -0.0 | -0.06 | -0.00 | 0.06 | 2454.6 | 32.7 | 13.120 | 2 | 5 | 1 | 2 | 1 | 1 | 4 | 1 | 0 | 20 |
| 20.19 | -385.6 | -467.6 | -80 | -0.0 | -0.01 | -0.00 | 0.04 | 2474.7 | 33.0 | 13.165 | 2 | 5 | 1 | 2 | 1 | 1 | 4 | 1 | 0 | 20 |
| 20.50 | -384.2 | -455.2 | -70 | -0.0 | 0.04 | -0.00 | 0.04 | 2460.9 | 32.8 | 13.209 | 2 | 5 | 1 | 2 | 1 | 1 | 4 | 1 | 0 | 20 |
| 20.80 | -382.5 | -444.2 | -60 | -0.0 | 0.10 | -0.00 | 0.10 | 2442.3 | 32.2 | 13.252 | 2 | 5 | 1 | 2 | 1 | 1 | 4 | 1 | 0 | 20 |
| 21.11 | -380.8 | -432.2 | -50 | -0.0 | 0.18 | -0.00 | 0.18 | 2417.1 | 31.9 | 13.312 | 2 | 5 | 1 | 2 | 1 | 1 | 4 | 1 | 0 | 20 |
| 21.64 | -378.8 | -420.8 | -40 | -0.0 | 0.25 | -0.00 | 0.25 | 2391.7 | 31.5 | 13.370 | 2 | 5 | 1 | 2 | 1 | 1 | 4 | 1 | 0 | 20 |
| 22.06 | -377.1 | -408.8 | -30 | -0.0 | 0.33 | -0.00 | 0.33 | 2365.2 | 31.2 | 13.428 | 2 | 5 | 1 | 2 | 1 | 1 | 5 | 1 | 0 | 20 |
| 22.48 | -375.3 | -397.1 | -20 | -0.0 | 0.41 | -0.00 | 0.41 | 2339.3 | 30.8 | 13.485 | 2 | 5 | 1 | 2 | 1 | 1 | 5 | 1 | 0 | 20 |
| 22.89 | -372.7 | -385.3 | -10 | -0.0 | 0.49 | -0.00 | 0.49 | 2313.1 | 30.0 | 13.542 | 2 | 5 | 1 | 2 | 1 | 1 | 5 | 1 | 0 | 20 |
| 23.31 | -370.1 | -372.7 | 10 | -0.0 | 0.58 | -0.00 | 0.58 | 2248.9 | 29.1 | 13.598 | 2 | 5 | 1 | 2 | 1 | 1 | 5 | 1 | 0 | 20 |
| 23.73 | -367.1 | -360.1 | 20 | -0.0 | 0.67 | -0.00 | 0.67 | 2179.6 | 28.1 | 13.653 | 2 | 5 | 1 | 2 | 1 | 1 | 5 | 1 | 0 | 20 |
| 24.15 | -364.1 | -347.1 | 30 | -0.0 | 0.76 | -0.00 | 0.76 | 2106.8 | 27.1 | 13.708 | 2 | 5 | 1 | 2 | 1 | 1 | 5 | 1 | 0 | 20 |
| 24.57 | -361.2 | -334.1 | 40 | -0.0 | 0.86 | -0.00 | 0.86 | 2032.8 | 26.1 | 13.762 | 2 | 5 | 1 | 2 | 1 | 1 | 5 | 1 | 0 | 20 |
| 24.99 | -357.9 | -321.2 | 50 | -0.0 | 0.96 | -0.00 | 0.96 | 1957.6 | 25.0 | 13.816 | 2 | 5 | 1 | 2 | 1 | 1 | 5 | 1 | 0 | 20 |
| 25.41 | -355.0 | -307.9 | 60 | -0.0 | 1.06 | -0.00 | 1.06 | 1878.5 | 24.0 | 13.869 | 2 | 5 | 1 | 2 | 1 | 2 | 5 | 1 | 0 | 20 |
| 25.83 | -351.2 | -295.0 | 70 | -0.0 | 1.16 | -0.00 | 1.16 | 1800.8 | 22.9 | 13.922 | 2 | 5 | 1 | 2 | 1 | 2 | 5 | 1 | 0 | 20 |
| 26.24 | -351.4 | -281.4 | 80 | -0.0 | 1.27 | -0.00 | 1.27 | 1716.0 | 22.0 | 13.974 | 2 | 5 | 1 | 2 | 1 | 2 | 5 | 1 | 0 | 20 |
| 26.66 | -347.8 | -267.8 | 90 | -0.0 | 1.38 | -0.00 | 1.38 | 1629.4 | 21.7 | 14.026 | 2 | 5 | 1 | 2 | 1 | 2 | 5 | 1 | 0 | 20 |

FIG. 7d

| HGT | DIST | POSN | RANGE | LAT | ELEV | AZ | ANGLE | EFF INT | P/C I | KM*-1 | BLOCKS TYPE | LEV | AN | INT | ELEMENTS LAP | LOG | HGT | LAT | TST |
|---|---|---|---|---|---|---|---|---|---|---|---|---|---|---|---|---|---|---|---|
| 27.06 | -343.9 | -253.9 | 90  | -0.0 | 1.50 | -0.00 | 1.50 | 1537.9 | 20.5 | 14.077 | 2 | 5 | 1 | 2 | 2 | 1 | 5 | 2 | 0 | 20 |
| 27.50 | -340.0 | -240.0 | 100 | -0.0 | 1.62 | -0.00 | 1.62 | 1444.5 | 19.3 | 14.128 | 2 | 5 | 1 | 2 | 2 | 1 | 6 | 2 | 0 | 20 |
| 28.02 | -333.9 | -223.9 | 110 | -0.0 | 1.80 | -0.00 | 1.80 | 1311.2 | 17.5 | 14.190 | 2 | 5 | 1 | 2 | 2 | 1 | 6 | 2 | 0 | 20 |
| 28.55 | -326.9 | -206.9 | 120 | -0.0 | 1.99 | -0.00 | 1.99 | 1162.1 | 15.5 | 14.253 | 2 | 5 | 1 | 2 | 2 | 1 | 6 | 2 | 0 | 20 |
| 29.07 | -317.4 | -187.4 | 130 | -0.0 | 2.23 | -0.00 | 2.23 | 975.2  | 13.0 | 14.314 | 2 | 5 | 1 | 2 | 2 | 1 | 6 | 2 | 0 | 20 |
| 29.60 | -299.1 | -159.1 | 140 | -0.0 | 2.65 | -0.00 | 2.65 | 682.7  | 9.1  | 14.375 | 2 | 5 | 1 | 2 | 2 | 1 | 6 | 2 | 0 | 21 |
| 30.12 | -295.3 | -145.9 | 150 | -0.0 | 2.81 | -0.00 | 2.81 | 649.7  | 8.7  | 14.435 | 2 | 5 | 1 | 2 | 2 | 1 | 6 | 2 | 0 | 20 |
| 30.64 | -292.3 | -132.3 | 160 | -0.0 | 2.99 | -0.00 | 2.99 | 614.7  | 8.2  | 14.495 | 2 | 5 | 1 | 2 | 2 | 1 | 6 | 2 | 0 | 20 |
| 31.17 | -288.7 | -118.7 | 170 | -0.0 | 3.16 | -0.00 | 3.16 | 578.9  | 7.7  | 14.554 | 2 | 5 | 1 | 2 | 2 | 1 | 6 | 2 | 0 | 20 |
| 31.69 | -284.5 | -104.5 | 180 | -0.0 | 3.36 | -0.00 | 3.36 | 539.3  | 7.2  | 14.612 | 2 | 5 | 1 | 2 | 2 | 1 | 6 | 2 | 0 | 20 |
| 32.22 | -280.0 | -90.0  | 190 | -0.0 | 3.56 | -0.00 | 3.56 | 497.2  | 6.6  | 14.670 | 2 | 5 | 1 | 3 | 2 | 1 | 6 | 2 | 0 | 20 |
| 32.74 | -274.5 | -74.5  | 200 | -0.0 | 3.80 | -0.00 | 3.80 | 449.0  | 6.0  | 14.727 | 2 | 5 | 1 | 3 | 2 | 1 | 6 | 2 | 0 | 20 |
| 33.27 | -267.2 | -57.8  | 210 | -0.0 | 4.10 | -0.00 | 4.10 | 389.0  | 5.2  | 14.784 | 2 | 5 | 1 | 3 | 2 | 1 | 6 | 2 | 0 | 24 |
| 33.79 | -225.8 | -5.8   | 220 | -0.0 | 5.51 | -0.00 | 5.51 | 154.7  | 2.1  | 14.840 | 2 | 5 | 1 | 3 | 2 | 1 | 6 | 2 | 0 | 19 |
| 34.31 | -229.7 | 0.3    | 230 | -0.0 | 4.00 | -0.00 | 4.00 | 11207.0 | 37.6 | 14.896 | 1 | 4 | 1 | 1 | 3 | 1 | 6 | 2 | 0 | 18 |
| 34.84 | -239.7 | 0.4    | 240 | -0.0 | 3.77 | -0.00 | 3.77 | 12369.0 | 41.2 | 14.952 | 1 | 4 | 1 | 1 | 2 | 1 | 6 | 2 | 0 | 18 |
| 35.36 | -249.7 | 0.3    | 250 | -0.0 | 3.56 | -0.00 | 3.56 | 13494.3 | 45.0 | 15.006 | 1 | 4 | 1 | 1 | 2 | 1 | 6 | 2 | 0 | 18 |
| 35.89 | -259.6 | 0.4    | 260 | -0.0 | 3.37 | -0.00 | 3.37 | 14482.8 | 48.3 | 15.061 | 1 | 4 | 1 | 1 | 2 | 1 | 6 | 2 | 0 | 18 |
| 36.41 | -269.6 | 0.2    | 270 | -0.0 | 3.19 | -0.00 | 3.19 | 15445.9 | 51.5 | 15.115 | 1 | 4 | 1 | 1 | 2 | 1 | 6 | 2 | 0 | 18 |
| 36.93 | -279.6 | 0.2    | 280 | -0.0 | 3.02 | -0.00 | 3.02 | 16296.3 | 54.3 | 15.166 | 1 | 4 | 1 | 1 | 2 | 1 | 6 | 2 | 0 | 18 |
| 37.46 | -289.8 | 0.2    | 290 | -0.0 | 2.87 | -0.00 | 2.87 | 17130.6 | 57.1 | 15.221 | 1 | 4 | 1 | 1 | 2 | 1 | 6 | 2 | 0 | 18 |
| 37.98 | -299.6 | 0.4    | 300 | -0.0 | 2.72 | -0.00 | 2.72 | 17869.8 | 59.6 | 15.274 | 1 | 4 | 1 | 1 | 2 | 1 | 6 | 2 | 0 | 18 |

APPARATUS FOR ESTIMATING SLANT VISIBILITY IN FOG

The present invention relates to apparatus for estimating the slant visibility in obscured atmospheres such as fog, falling snow and rain, and in particular for providing an indication for use by aircrew and air traffic controllers as to when, during an aircraft landing approach in fog conditions, the pilot is likely to be able to see the runway lights and a extent to which airport lighting pattern or marking will be capable of being viewed by the pilot as the runway approach progresses. The mode of development of this extent during the course, say, of an aircraft landing run, is called a visual sequence.

Hitherto operational measurements of low visibility for assisting air traffic control have almost always been made by human observers or instruments, such as transmissometers, close to the ground. These measurements are reported as 'runway visual range'. This technique cannot usually give a reliable indication of any vertical element to visibility, and this vertical element has a profound effect upon what is called the slant visual range, that is for example, the distance an aircraft pilot can actually see when looking toward the ground, anywhere between directly below and the horizon. The ground measurement derived runway visual range then is used to estimate the probability of a landing success. The shortcomings of this ground measurement deviation method is that in the interest of safety, visual landing attempts are prohibited more often than might have really be necessary. This is because the majority of low visibility situations are those involving a deep mature fog or a low cloud, and since fog density increases with altitude (up to a relatively instantaneous ceiling), once a pilot has made visual contact with a runway lighting pattern he will be able to maintain it down to the landing. The ground measurement deviation method does not, of course, endeavour to imply any actual estimate either of the visual contact height or of the visual sequence. Moreover it can not made allowance for shallow, developing, dispersing or lifting fogs, which although being perhaps less prevalent than deep mature fogs are nevertheless frequently encountered.

Drawbacks also exist in the measuring technique per se. This has customarily comprised deploying transmissometers with horizontal measuring paths at a standard measuring height of 5 m above the ground (5 ft in the UK). Shallow ground radiation fog the ceiling of which is below transmissometer level will not be detected. A fog ceiling slightly above transmissometer level will result in an unduly severe fog indication and an unnecessary refusal being issued to the pilots of tall aircraft, (eg those where the cockpit is over 10 m from the ground). Furthermore a fog ceiling intermittently penetrating the measurement path of the instrument will result in large and quite illusory fluctuations of the reported values.

It will also be appreciated that there are, to say the least, constraints pertaining to the deployment in the vicinity of airfields of instrumentation operating at significant heights, especially heights where at instrumentation could be employed to simulate meaningfully slant visual range.

What has now been discovered is that by making a small number of slant or vertical measurements (typically three in number) from various heights to the ground sufficient information is available which by the judicious application of predetermined models of mean extinction coefficient profile allow estimation of the actual profile over a range of heights not less than that of the measurements with a useful accuracy. (Extinction coefficient ($\sigma$) is the reciprocal of the distance over which light falls, due exclusively to obscuration, to 1/e times its original intensity.

Accordingly, in those circumstances where the fog or cloud extends considerably above the ground (several hundreds of feet) then the mean extinction coefficient profile in the bottom one hundred or so feet may be adequately described by the use of a polynomial of order two or less such that $$\bar{\sigma}_{h1} = \frac{1}{h_1} \int_{h=o}^{h_1} \sigma_h \, dh \simeq a h_1^2 + b h_1 + c$$

where
$\bar{\sigma}_{h1}$ is the mean integral of extinction coefficient between the ground and a height$=h$,
$\sigma_h$ is the extinction coefficient at a height h
a, b and c are constants
accordingly 3 values of $\sigma$ at the heights $h_1$, $h_2$, $h_3$ will determine a, b and c.

In those cases where the upper extent of the fog or cloud is below the upper limit of measurement one may proceed by determining the height of the nominal fog top in relation to the heights of the slant or vertical measurements and then to model separately the profile of the mean integral of extinction coefficient both below and above the fog top. Although the three measurements are apportioned between the two now independent models of mean integral of extinction coefficient, it has been found that models of a lesser complexity are of value in those cases, viz:

$$\bar{\sigma}_{hL} = jh + k$$

below the fog top and $$\bar{\sigma}_{hu} = \frac{p}{(qh + r)}$$

above the fog top, where j, k, p, q and r are constants.

Where the fog top lies between the upper two fog measurements only one point is available for the calculation of $\bar{\sigma}_{hu}$ and an assumption can be made about r which generally improves the performance of the model compared to removing r from the model.

In the case where the fog top lies between the lower pair of measurement heights (upper extent of individual slant or vertical) only one value is available for the calculation of $\bar{\sigma}_{hL}$ and in this case the term jh is ignored. The cusp resulting from the intersection of these two models at the nominal fog top may additionally be abated.

According to one aspect of the present invention therefore apparatus for estimating a fog structure comprises a transmissometer array disposed for slant operation at different heights above the ground, and means for employing signals derived from the transmissometer array in estimating slant visual range. By slant operation is meant that the points between which the extinction coefficient are measured are one above, but not necessarily vertically above, the other.

A transmissometer generally comprises a light source and a detector of light intensity over a given distance from the source. Rather than have, however, a source in one unit and a detector in another it is convenient if the said other unit is a reflector. In this manner the source/detector unit can readily be arranged so that the detector unit compares the intensity of both the emitted and the reflected light. This arrangement is particularly suitable in the present invention, as it permits a transmissometer source/detector unit array to be mounted close to the ground, where it can readily be serviced, and reflectors to be mounted at different heights. The source/detector unit array may comprise a single unit, a composite of several units, or several (in particular three) distinct units.

It is an important feature of the present invention, from the point of view particularly of cost, that the apparatus may be arranged to provide readings at three different heights, and preferably comprises three reflectors, one at each of the heights, and a source/detector unit at ground level.

It is preferred not to use a single reflector traversing the heights, for simultaneous readings are preferred and the traverse movement will usually give rise to eddies which will affect the readings.

Means for keeping the source and/or detector clean may also be provided. These preferably comprise air curtains and a shield tube, though washing and wiping means may additionally or alternatively be employed. It may be preferred, for the purpose of both realism and equipment hygiene, for the light paths not to be vertical.

According to a feature of the invention the means for employing signals derived from the transmissometer array in estimating the slant visual range may comprise means for converting the transmissometer signals into signals representing the mean integral of extinction coefficient ($\overline{\sigma}_h$) over the associated distance, means for comparing the $\overline{\sigma}_h$ signals and selecting an appropriate model from a predetermined set of models, means for determining the values of the constants in the selected model, and thence the definitive models, and means for deriving an estimate of the mean integral of extinction coefficient profile from the definitive models.

The means for converting the transmissometer array signals into $\overline{\sigma}_h$ signals may employ the function:

$$\overline{\sigma}_h = \frac{1}{-R} \text{Log}_e \frac{I_h}{I_o}$$

where
R is the distance over which the measurement is taken,
$I_h$ is the signal from the transmissometer, and
$I_o$ is a clear day datum transmissometer signal.

The predetermined set of models may comprise:

$\overline{\sigma}_h = ah^2 + bh + c$ for use when $\overline{\sigma}_{h3} > \overline{\sigma}_{h2} > \overline{\sigma}_{h1}$, $\dfrac{p}{qh_3 + r}$ and $j(h_2$ or $h_1) + k$ for use when $\overline{\sigma}_{h3} < \overline{\sigma}_{h2} > \overline{\sigma}_{h1}$, and $\dfrac{p}{q(h_3 \text{ or } h_2) + r}$ and $k$ when $\overline{\sigma}_{h3} < \overline{\sigma}_{h2} < \overline{\sigma}_{h1}$.

Typically, heights from the ground, over which the $I_h$ signals can be derived, may be 4, 12, 30 meters, so that the reflector units may be mounted on a tower 30 meters high, which, in accordance with the above-mentioned current regulations, may be sited 370 m laterally from the centreline of any airfield runway. The $\overline{\sigma}_h$ profile may be extrapolated to a small amount, eg 10-20% above the maximum height ($h_3$).

A lower measuring base may be sited closer to the runway for deriving an $I_h$ signal at, say, 4 meters height to provide some confirmation of fog extent and consistency and to improve the estimate of the $\overline{\sigma}_h$ profile.

The apparatus may further have means for determining slant visual range and visual sequence from the $\overline{\sigma}_h$ profile, that is to say the distance from and position with respect to, the runway lighting array at which the pilot will see some part of that array, how much he should be able to see, and how his acquisition will develop in the course of the landing (visual sequence).

The determination of a visual contact height (the height at which a descending aircraft pilot will first see the landing lights) and a visual sequence, requires consideration of, in addition to the fog structure, the lighting intensity, pattern and direction, the pilot's visual threshold, the structure and configuration of the aircraft, the amount and constitution of day or night light, and the aircraft cabin lighting.

It may be possible to derive for certain airfields a function:

$$H_c = \frac{\gamma(\log_{10} E_T)^\alpha}{\overline{\sigma}_{hc}}$$

where
$H_c$ is the visual contact height,
$\overline{\sigma}_{hc}$ is the mean integral slant extinction coefficient at that height,
$\gamma$ and $\alpha$ are empirical constants, related to flight path and lighting pattern characteristics respectively,
and $E_T$ is the eye illuminance threshold (measured in lux).

This function was derived from Allards's law which states:

$$E_T = \frac{I}{R^2} e^{-\sigma R}$$

where I is the intensity of a point source of illumination, and R is the visual range to extinction, by determining a number of visual sequence patterns for a particular flight path in different fog and eye illuminance threshold situations.

The apparatus may therefore have means for determining the intersection of the $H_c$ function and the definitive model, this intersection occurring at $H_c$. For circumstances where the eye illuminance threshold is not known the apparatus may have means for deriving $\text{Log}_{10}(E_T)$ from the function:

$$Log_{10}(E_T) = u \, log_{10}\beta - v$$

where $\beta$ is background brightness in nits and u and v empirical constants typical values for which are 0.675 and 5.7 respectively. $\beta$ may be derived from a detector mounted at the top of the transmissometer tower.

In these circumstances the apparatus may be arranged to feed only $\text{Log}_{10}(E_T) \geq -w$ into the $H_c$ function, w being an accustomation factor for night use, typically 6.1.

The apparatus may additionally have means for storing aircraft configuration information, in particular information on the extent to which a particular aircraft in a landing run configuration obstructs the downward view of a pilot, applying this information to the derived $H_c$ value, and modifying $H_c$ accordingly.

It may be more appropriate in certain cases for the apparatus to have means for determining the slant visual range and the visual sequence rather than or in addition to $H_c$. A suitable method of determining slant visual range is iterative, involving applying the derived definitive $\bar{\sigma}_h$ model, the particular lighting pattern, direction and intensity and visual threshold values at a sequence of aircraft positions during a landing run. This method is described in Royal Aircraft Establishment Tech Memo Avionics 185 (BLEU) entitled "A Method of Computing the Visual Range of Lighting Patterns During the Approach to Landing" by A Puffett, August 1974. The apparatus may therefore have means for carrying out this method.

A second aspect of the invention provides processes for estimating a fog structure, and perhaps visual contact height, slant visual range and visual sequence, by operation of the means specified above.

By virtue of the present invention, then, a much more accurate assessment can be obtained than hitherto available of the slant visual range and visual sequence of the pilot of an aircraft approaching a runway in order to land. Moreover it has been found that significant discrepancies between the estimated values and the values in practice occur only briefly during transient conditions such as fog decay. Thus it should be possible, by means of the invention, to permit aircraft to land much more frequently in fog conditions than hitherto. Moreover the apparatus can readily be adapted to give visibility indications for such other obscuration conditions as snow and rain.

Figure 2:
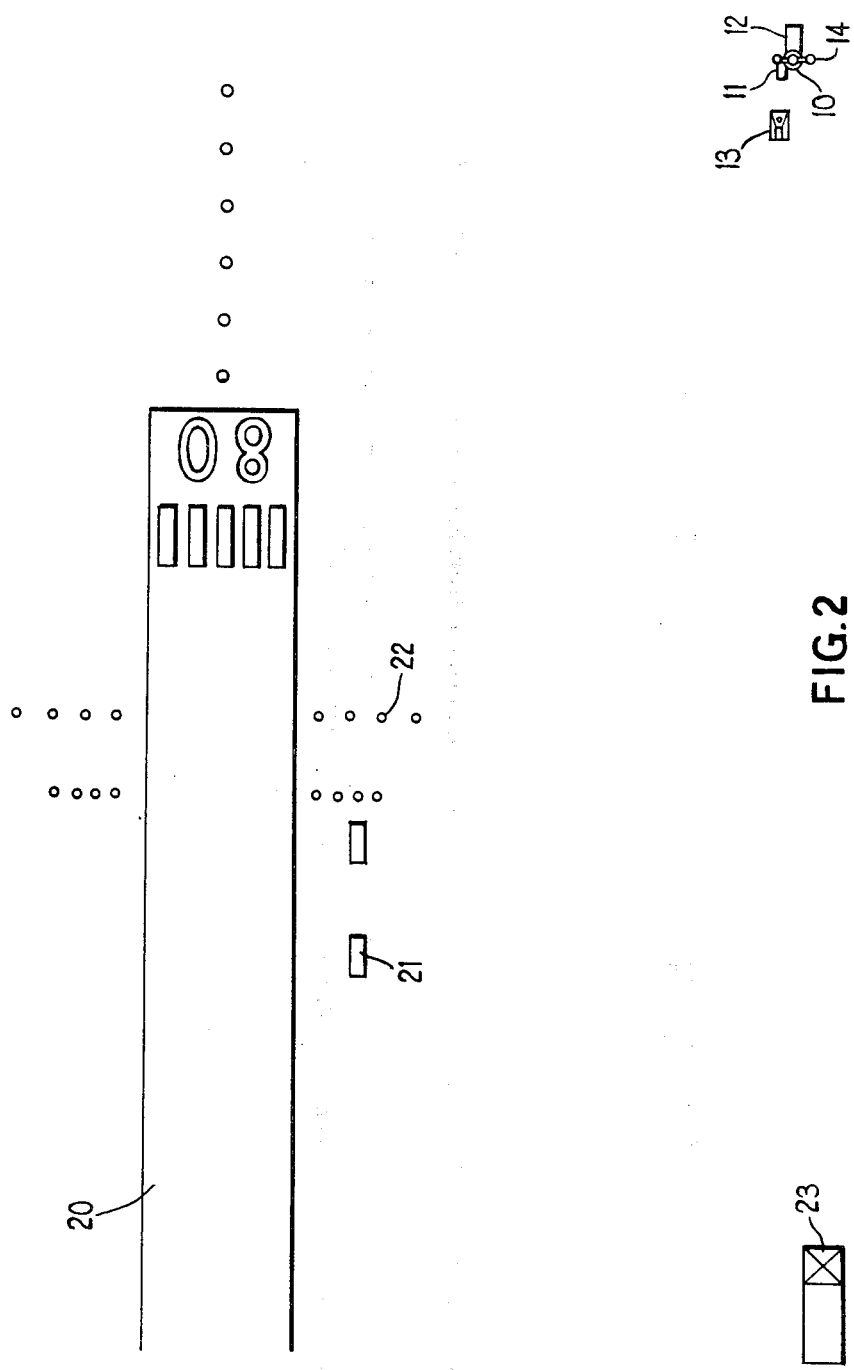
Figure 3:
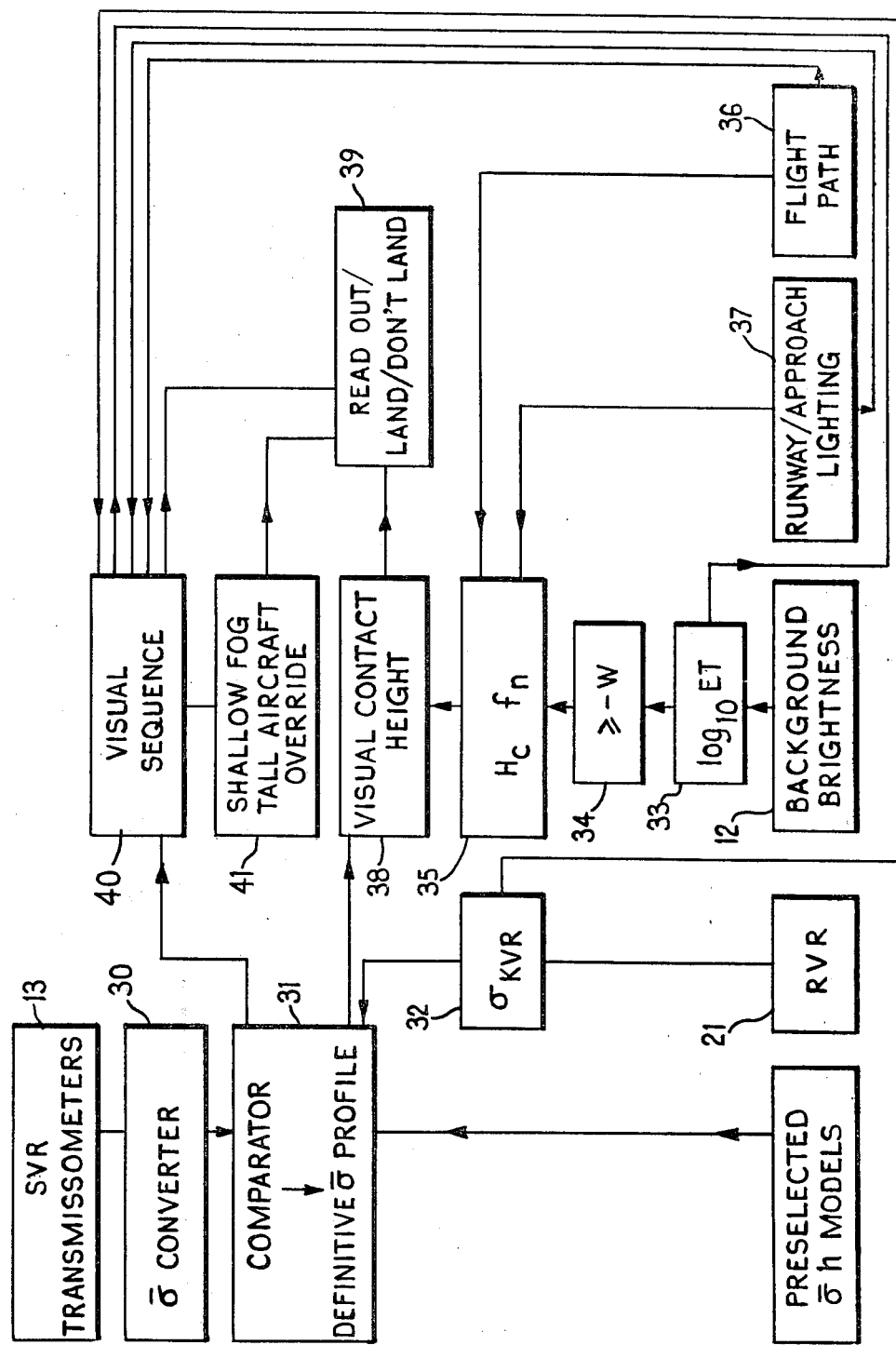
Figure 4A:
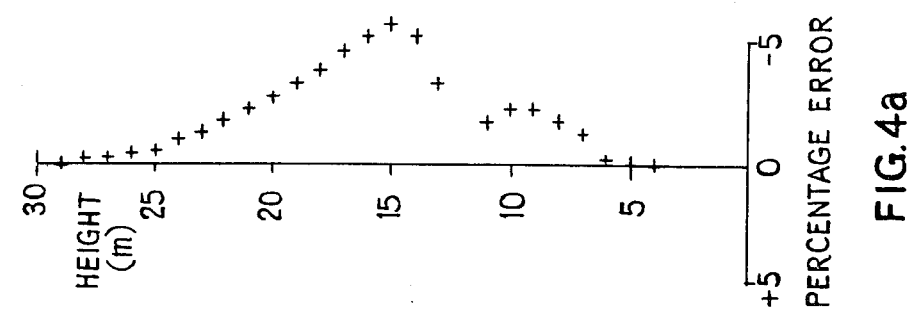
Figure 4:
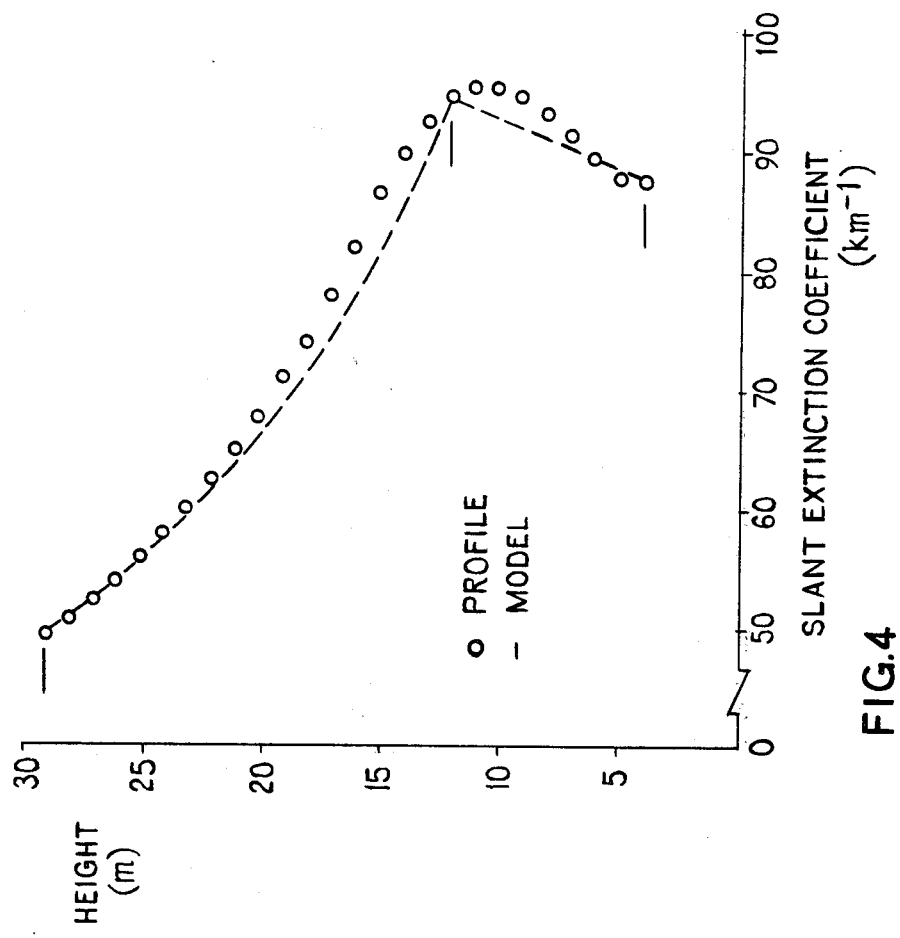
Figures 5, 5A:
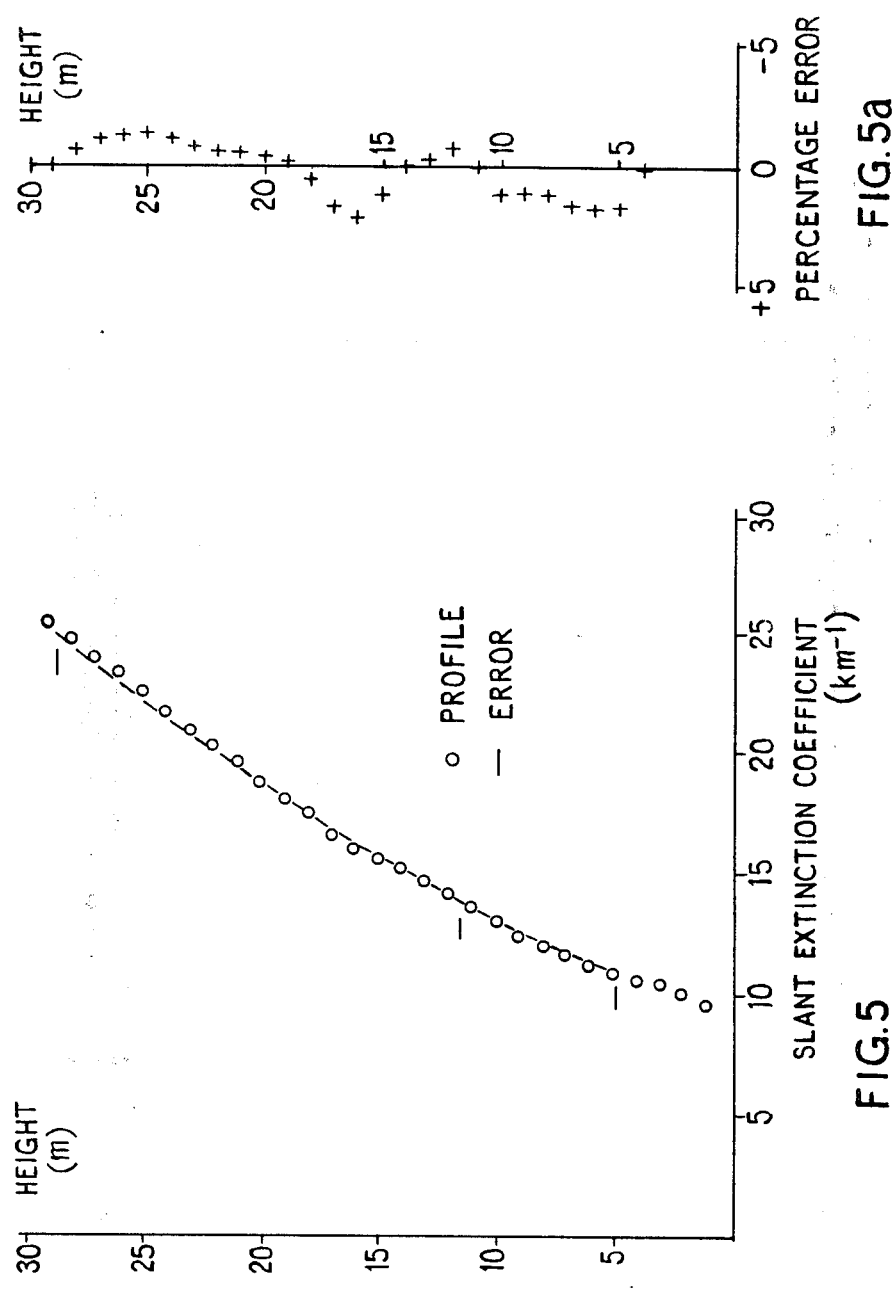
Figure 6A:
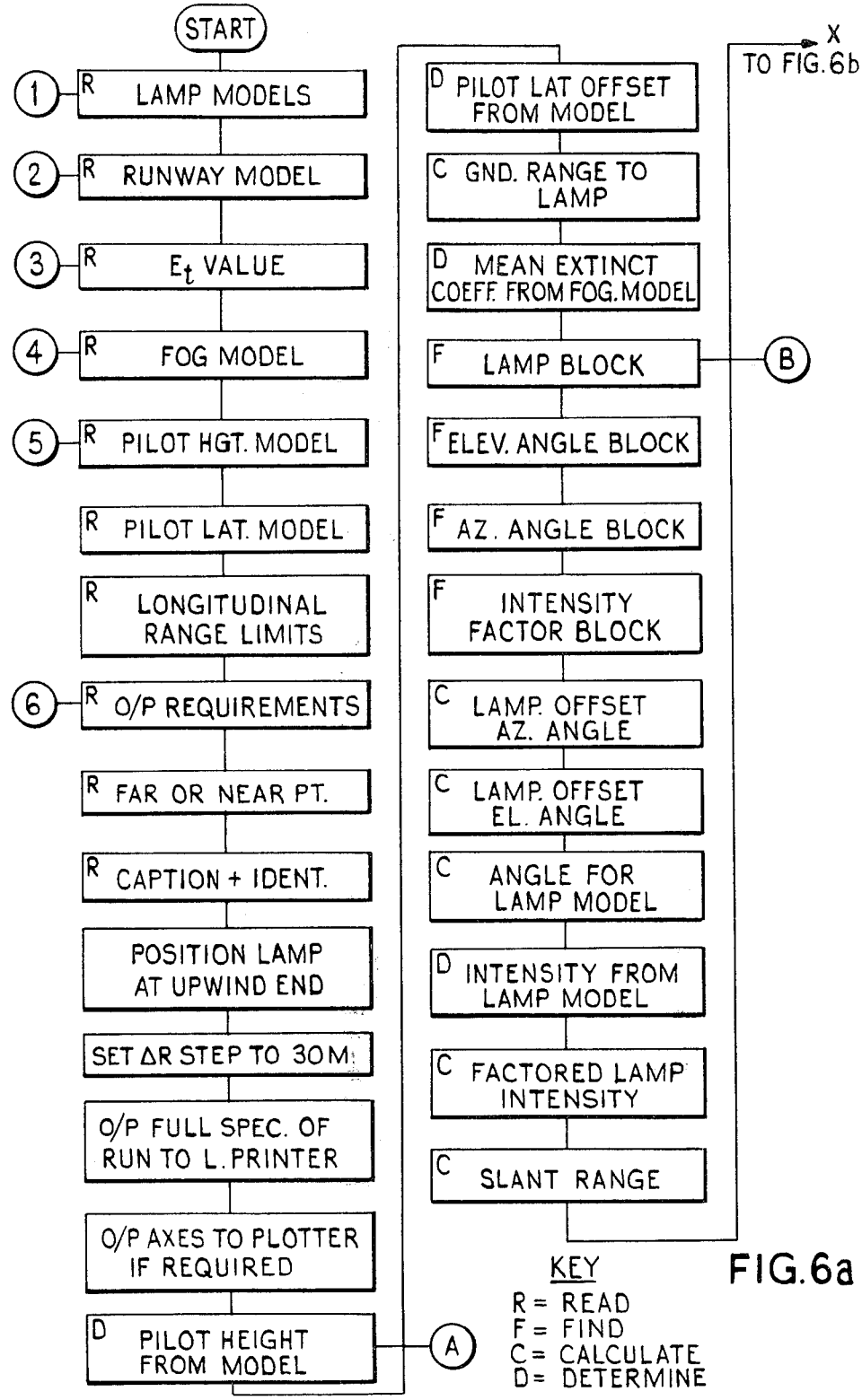
Figure 6B:
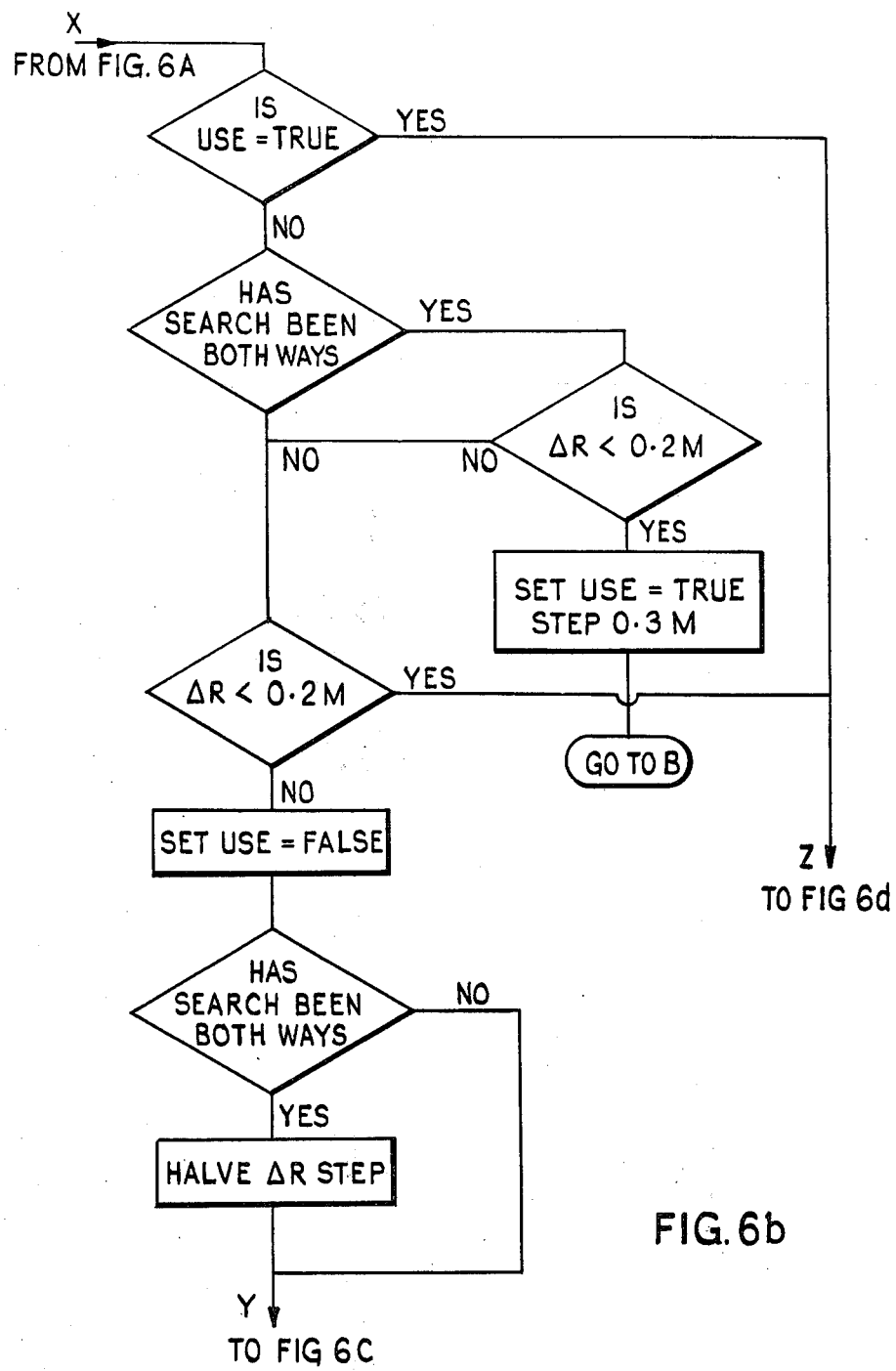
Figure 6C:
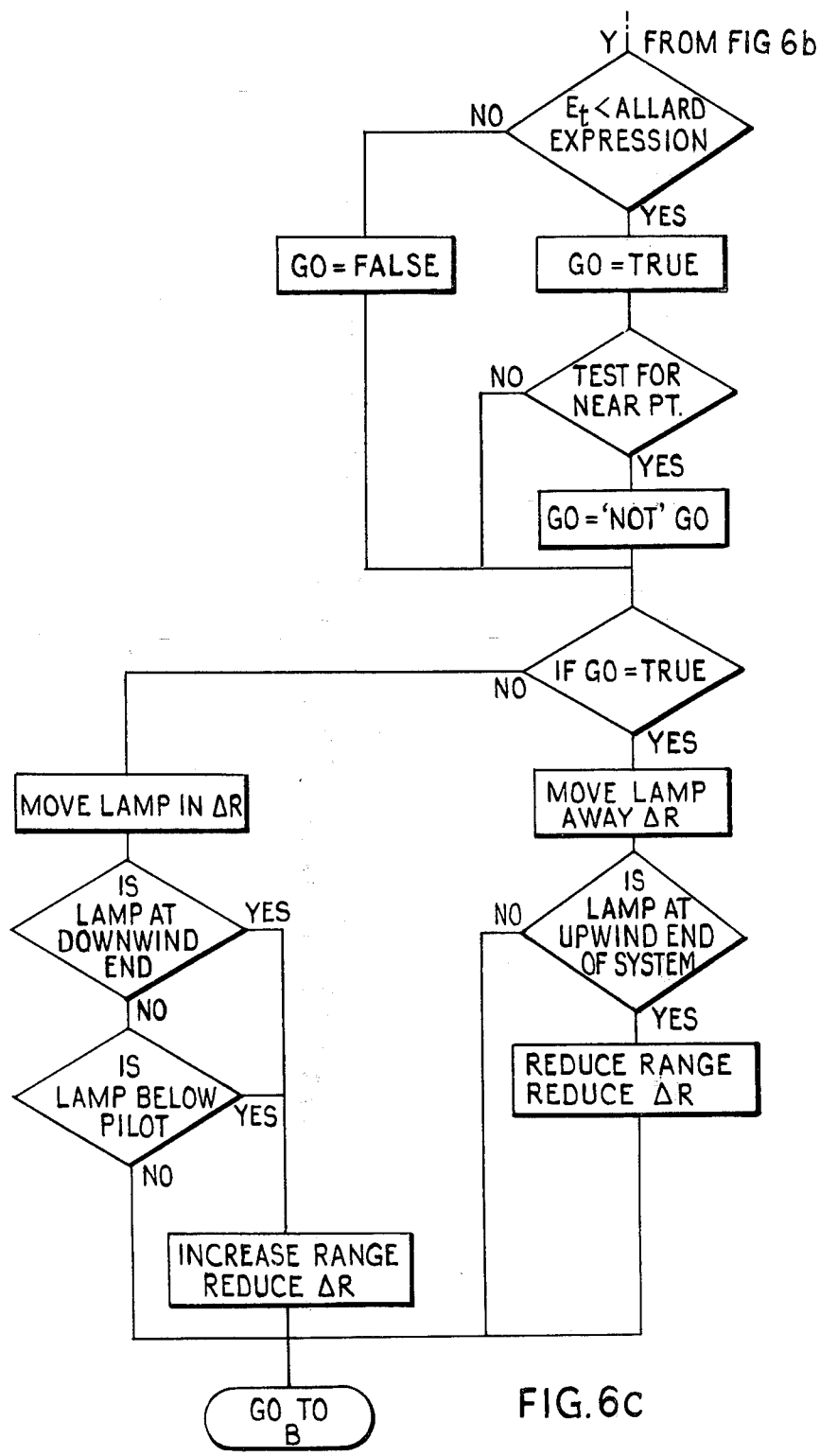
Figure 6D:
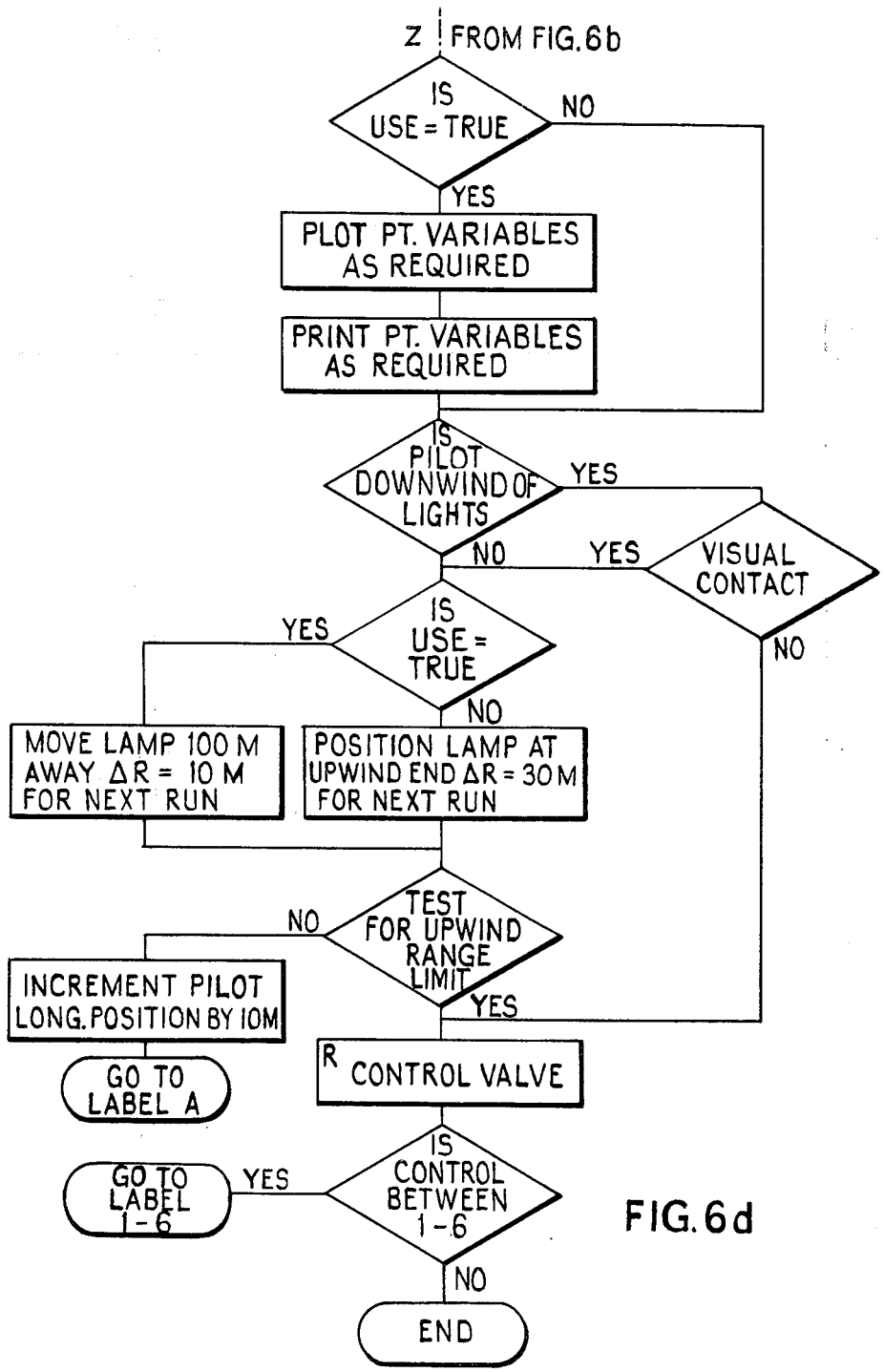

Apparatus for estimating slant visibility in fog will now be described by way of example with reference to the accompanying drawings, of which:

FIG. 1 is a schematic arrangement of a transmissometer array,

FIG. 2 is a plan view of a runway threshold environment including the transmissometer array, FIG. 3 is a flow chart depicting operation of the apparatus, FIG. 4 is a graph comparing experimentally derived and model extinction coefficient curves in shallow fog, FIG. 4a is a graph demonstrating the deviation of the shallow fog model from the empirical values, FIG. 5 is a graph comparing experimentally derived and model extinction coefficient curves in deep fog, FIG. 5a is a graph demonstrating the deviation of the deep fog model from the empirical values, FIGS. 6a-d comprise a generalised computer program flow chart for determining visual sequence, and FIGS. 7a-d comprise a tabulated output example of the program of FIGS. 6a-d.

FIG. 1 shows the principal data source, the Slant Visual Range (SVR) transmissometer array tower 10 carrying three transmissometer reflectors 11 at 4, 11 and 29 meters respectively, and a background brightness detector 12 at the top of the tower 10. Based on the ground a short distance from the tower 10 is a transmissometer 13 of the source/detector unit type. The tower also carries obligatory warning lights 14.

As illustrated in FIG. 2 the tower 10 is located 370 meters laterally from the centre of a runway 20 and 350 meters ahead of the threshold thereof.

A runway visual range (RVR) transmissometer array 21 is located 190 meters from the runway centre line and behind an approach lighting array 22. It is disposed for level operation at 5 meters height. A computer for processing signals from the SVR and RVR detectors is located in a control tower 23.

The process by which the computer derives visibility information using the RVR and SVR inputs is illustrated in FIGS. 3 to 5. As shown in FIG. 3 SVR transmissometer signals are converted to extinction coefficient signals $\bar{\sigma}_{h1}$ (4 m), $\bar{\sigma}_{h2}$ (11 m), $\bar{\sigma}_{h3}$ (29 m) in the converter 30, which signals are passed to a comparator element 31 of the computer. The computer has been preprogrammed with extinction coefficient ($\bar{\sigma}_h$) function models as follows:

$\bar{\sigma}_h = ah^2 + bh + c$ for use when $\bar{\sigma}_{h3} > \bar{\sigma}_{h2} > \bar{\sigma}_{h1}$, $\dfrac{p}{qh_3 + r}$ and $j(h_2$ or $h_1) + k$ for use when $\bar{\sigma}_{h3} < \bar{\sigma}_{h2} > \bar{\sigma}_{h1}$, and $\dfrac{p}{q(h_3 \text{ or } h_2) + r}$ and $k$ when $\bar{\sigma}_{h3} < \bar{\sigma}_{h2} < \bar{\sigma}_{h1}$.

For deep fog conditions, such as illustrated in FIG. 4, when the second order polynominal applies, a signal $\bar{\sigma}_{RVR}$ derived (at 32) from the RVR detector 21 is employed to determine the constant 'c'. FIG. 5 clearly illustrates the second of the above conditions, shallow fog, when two different expressions for $\bar{\sigma}_h$ are applied.

In the comparator 31 the computer compares $\bar{\sigma}_h$ with $\bar{\sigma}_{RVR}$ and selects the worst case $\bar{\sigma}_{hwc}$, selects in accordance with the relation one to another of $\bar{\sigma}_{hwc}$, $\bar{\sigma}_{h2}$ and $\bar{\sigma}_{h3}$, which of the above models is appropriate, and determines the remainder of the constants (including assuming a value for the constant r in cases where the fog ceiling is between 11 and 29 m) and hence a definitive $\bar{\sigma}_h$ profile.

From the background brightness detector 12 is derived a signal which is converted (at 33) into a function of eye illuminance threshold $E_T$ according to the formula:

$$Log_{10} E_T = u \, log_{10} \beta - v$$

The inventor used the value 0.675 and 5.7 for the empirical constants u and v respectively, but others skilled in the art are known to use higher values.

A discriminator 34 then determines whether $Log_{10} E_T$ should be passed on as such or limited to a minimum value w quantifying night time accustomisation factor. The inventor uses $w = -6.1$ but others skilled in the art may prefer a different value.

The chosen signal for $Log_{10} E_T$, is fed into a visual contact height $H_c$ function determining element 35. The visual contact height function is:

$$H_c = \dfrac{\gamma (\log_{10} E_T)^\alpha}{\sigma_{hc}}$$

as mentioned earlier in the specification, where $\gamma$ and $\alpha$, are empirical constants representing a particular flight path and lighting pattern (37). In one context their values were 288.7 and 1.3 respectively.

Together with the definitive $\bar{\sigma}$ profile from the comparator element 31 the visual contact height function $H_c$ is fed into a visual contact height estimating element 38, and the intersect, which occurs at the definitive $H_c$ estimate, is fed to an information output 39, thus providing a rapid, relatively inexpensive, and in some cases sufficient indication of when, during an approach to land, an aircraft pilot can expect to see the runway lighting.

As an adjunct or alternative to estimating a visual contact height using the function for $H_c$ and the elements 35 and 38 as described above, the apparatus has a visual sequence estimator element 40 for providing an estimate of the development of a pilot's visual acquisition of a runway and its lighting pattern during the course of a landing run. In one example the estimator element 40 comprises an Elliot 4100 computer to which can be configured a visual sequence program written in Algol 60 as now described below.

In order to simulate the lighting pattern and the conditions under which it is viewed, a number of models are needed to define the various parameters. These fall into two categories; those representing variables which are normally continuous functions such as the distribution of light in the beams of the different airfield lights, the vertical profile of fog density, and the path in space traced by the pilot's eyes. Each of these variables is modelled by a series of straight lines as detailed in Appendix D below. However it is necessary to use discrete values to describe the configuration of the ground lighting system, ie the disposition of the various types of lamps on the ground, and their associated setting angles. The adjustment of the intensity of portions of the lighting systems has to be similarly described.

In the present version of the program the lights are assumed to have two optical axes of symmetry and the distribution of light to be such that it may be represented in an isocandle diagram by a series of concentric ellipses of constant eccentricity. The consequence of these simplifying assumptions is that a lamp is fully described by one half of its vertical-axis light distribution and the ratio of the major and minor axes of the ellipse. Alternatively other beam characteristics such as may be represented by rectangles or ellipses of varying eccentricity can be easily incorporated.

In the present scheme the light output characteristics of each type of lamp is defined, as described in Appendix A, by five segments and in the examples considered this has adequately described the light distribution down to approximately two orders of magnitude below the peak value. This level of light has been found to be equivalent to off-axis viewing angles far in excess of those which are desirable in practice. No restriction has been placed on the number of lamp types so that a virtually unlimited number of types may be read into the program and called upon either in mixed lighting patterns or in differing successive cases.

Since this program is concerned with the conspicuity of the lamp fittings rather than with the information contained within the pattern itself, only a single line of lights is considered at any one time. That is to say a single line of lights lying in the ground plane and parallel to the centre line or X axis. However, where a comparison is required between the visual sequences produced by lights at differing lateral positions (ie runway centreline and runway edge lights) this may be achieved by the execution of a succession of cases, as is made clear below.

The various parameters associated with the lamps are their type, elevation and azimuth setting angles, and the intensity factor. This latter parameter allows the simulation of sub-standard sections of the lighting pattern as will be found necessary in practical examples. However, all the parameters are independent in terms of their applicability to a given longitudinal section of the pattern. Consequently each parameter must be separately defined over the whole length of the pattern. This is achieved by defining the downwind end of the pattern and assigning a value to the parameter. This value is then assumed to hold for increasing upwind positions until restated, or until the upwind end of the pattern is reached. In this way a series of blocks of values for a parameter may be built up, the only restriction being that the minimum distance over which a parameter can be assigned a particular value is 10 meters. This distance is the size of the step currently in use for scanning along the lights, thus any block of smaller length might be passed over without its presence being recognised. Whilst smaller step intervals may be used the resulting increase of computational time may prove unacceptable.

If it should be required to introduce gaps into the lighting pattern this may be achieved in several ways, one being by the definition of a dummy light model having zero intensity; another method is that of modifying one of the existing lighting models by a zero intensity factor. The former method may be preferred since this is more readily identified in the subsequent output data.

The major visibility conditions which dictate the range at which a given light can be seen, are the illuminance threshold of the pilot's eyes and the effective mean extinction coefficient of the atmosphere between the pilot and the ground.

In the present version of the program the illuminance threshold is single-valued, whereas in practice this is a variable dependent not only on the quantity of fog between the pilot and the ground in the direction of view, but also on the direction of view in terms of the veiling illumination due to the sun by day and to the ground lighting in the pilot's near field by night.

The parameter which represents the attenuation of the atmosphere is that of the mean extinction coefficient which is derived from the definitive $\overline{\sigma}_h$ profile.

The path of the pilot's eyes is defined in terms of height above the ground and lateral displacement from the centreline. Both the models are of the segmented-line type as mentioned above and described in Appendix A. In addition, limits for the excursion in longitudinal position are given. These enable the pilot's motion to be restricted to that portion of the approach or landing which gives information relevant to the case in hand.

As a matter of convenience these models are organised with the elements commencing at the upwind and running end back towards the approach, so that in effect the pilot flies backwards up the approach path.

When it is required to run cases involving offset viewing or curved flight paths sign conventions assume some importance. In order to facilitate the construction and interpretation of cases all spatial coordinates are referred to ground axes. The choice of the origin is somewhat arbitrary, however, the use of the intersection of the runway centreline with either the runway threshold or glidepath origin will generally be the most convenient. The convention adopted is that the downwind end of the pattern, a lateral displacement to the right (when viewed from the downwind end), and the pilot eye height are all positive.

When considering lamp setting angles a change to local axis is effected (for convenience of implementation). The convention is such that azimuth angles are referred to a line parallel to the centreline and positive to the right when looking downwind. Whilst the elevation angle is considered positive, it should be noted that the lamp is set in azimuth before the elevation angle is applied. The described sign conventions follow the approach normally adopted by engineers in considering airfield lighting.

As has been stated above, a number of models must be defined and variables specified before the program can be run. In order to minimise the work necessary to assemble the data the models are organised in the following order: lamp, models, lighting pattern, illuminance threshold, fog model, pilot eye path models and finally program controls. Thus, for instance, changes can be made to the fog model without having to re-enter the lamp and pattern models. This is achieved by the provision of a number of entry points in the program so that for a succeeding case only the data for the models requiring change and those following in the list need to be entered. The constructions and format of input data for a single run is shown in Appendix B. This may be compared with actual input data, an example of which is shown in Appendix C. It should be noted that apart from the caption, only the numbers in Appendix C have any significance for the computer and that the headings merely serve to break up the numbers into more recognisable groups. Examination of Appendix C will reveal the numbers to be of both REAL and INTEGER typr. The variables have been defined by type in Appendix B, since with the exception of $LT_{NT}$ in the lighting pattern, integers are unsubscripted. A further point of interest is the use of the variable $R_p$ in the lighting pattern, which serves to close all the parameter blocks in the lighting pattern on their upwind side. It will be seen that both Appendix B and Appendix C include a section labelled CASE, a description of which is below:

If it is assumed that input data has been read then the general method of determining the position of the limit of vision is as follows:

The upwind limit of X which is the pilot's initial longitudinal position is used to determine the lateral position and height from the eye path models. The height is then used to determine the mean extinction coefficient to the ground by means of the fog model. For this initial position of the pilot a search is made along the ground from the upwind end of the pattern and parallel to the centreline at 30 m intervals. At each such point on the ground the appropriate light is positioned and given the required setting angles.

The cartesian coordinates of the pilot are then calculated with respect to the angled and tilted lamp axes, so that the pilot's bearings may be determined as azimuth and elevation angles relative to the principal axes of the lamp. By this means the effective intensity directed towards the pilot can be calculated using the relevant lamp model. This value is then factored as required and substituted together with the slant range and the mean extinction coefficient into the equation for Allard's Law. The resulting eye illuminance is then tested against the stated illuminance threshold.

Once a ground position has been found where the eye illumination exceeds the threshold value, ie a lamp is visible, then the step size is reduced and the direction of the search reversed. This procedure is repeated until two successive points are within 0.2 m. The ground position is now moved 0.3 m in the direction of increased eye illumination and the various parameters calculated as before, these values being the ones used as output data. The pilot's eye is now moved to a new position 10 m further downwind and the procedure is repeated. Slight modification of the procedure occurs when visual contact was achieved for the pilot's previous position (which is the normal situation) in that the initial search step is reduced from 30 m to 10 m and the search commences 100 m upwind of the previous ground position. This allows a generally better resolution of the visual sequence at initial contact without any increase in the computation time. The present version of the program gives a solution of Allard's law to within 0.3 m after approximately 20 iterations. This occupies a computation time of approximately two thirds of a second. It should be noted that the ground positions determined do not, in general, relate to the actual position of lamps, rather where such a lamp should be placed for threshold eye detection. However, the computed results do allow the actual positions of lamps to be considered retrospectively.

Measures are taken to combat a number of anomalous situations that may arise during the search procedure. Such conditions include the visual range being dictated by the extent of the lighting pattern rather than by the visibility, and a complete absence of visual contact because the pilot is either too high, or too far downwind for the prevailing conditions, or upwind of all lights.

In addition, an alternative mode of operation permits the determination of the nearest visible light. Once visual contact has been established as has been described the search is continued with the discriminants reversed so that threshold eye illumination is sought for a nearer lamp. In this way a more realistic picture can be built up of the extent to which the lighting pattern is visible since both the far and near points of vision are known.

To further elucidate the operation of the program a generalised flow chart is shown in FIG. 6. This figure outlines the complete process from the reading of the input data to the termination of the program. In order to prevent confusion some labelled entry points have been substituted in place of flow paths. It should be pointed out that the name of the logical variable 'GO' has no intrinsic meaning, but the logical variable 'USE' is employed to indicate the suitability of data for output purposes. Explanations of the code letters used in some of the boxes may be desirable since particular meaning has been given to the words in the key. Read is used to denote the reading of the appropriate input data, while find means that a value is read directly from the stored model. This latter contrasts with the use of determine which implies that some calculation is required in order to obtain the required value from the model. Finally calculate alludes to the evaluation of algebraic expressions not directly linked with the input models.

Facilities exist for both the tabulation and plotting of certain of the variables. However, to avoid possible confusion each case produces a tabulation of all the defining input models and parameters (Appendix D), irrespective of the current form of output employed.

The tabulated output data includes all basic parameters and, if required, the current states of all models at the completion of each search (FIG. 7). Briefly, the interpretation of the columns in FIG. 7 is as follows:

1. Height of the pilot's eyes above the ground plane (meters).
2. X component of separation between the lamp and the pilot (meters).
3. X position of the lamp ⎫
4. X position of the pilot ⎬ ground axes (meters).
5. Lateral separation (Y) between the pilot and the line of lights (meters).
6. Elevation angle of the pilot ⎫
7. Azimuth angle of the pilot ⎬ in lamp axes (degrees).
8. Angle resulting from (6) and (7) uses to determine intensity (degrees).
9. Value of intensity from lamp model by application of (8) (candles).
10. Intensity expressed as a percentage of the peak value of that lamp.
11. Mean extinction coefficient along the vertical path between the pilot and the ground ($km^{-1}$).

The remaining columns indicate which defining blocks and elements in Appendix C or Appendix D apply to the particular solution, whilst the column marked TEST uses a zero to indicate the satisfactory solution of Allard's law. In addition output is suppressed for those pilot positions when no visual contact was achieved. Finally, the right hand column shows the number of iterations required to achieve the resolution of 0.5 m.

The examples shown in Appendix D and FIG. 7 and derived in part from Appendix C apply to a simple case where both the line of lights and the pilot are placed on the centreline. As a consequence no results have been obtained for the azimuth offset angle (col 7 in FIG. 7). However, persons skilled in the art will, in view of the above, readily perceive how they can be obtained.

APPENDIX A

A number of models are required within the program and a standard technique has been applied. Parameters which may require approximations to be made to continuous functions are the polar distribution of light about the principal axis of a lamp, the vertical gradient of fog density, and the pilot's eye height and lateral position.

An approach to modelling which is both easy to comprehend and implement, is that of the segmented straight line approximation. Since data sources for the models will inevitably be diverse in nature ranging perhaps from a few discrete points to highly accurate continuous functions it is suggested that the segments are fitted by eye to graphical plots of the source data.

It should be noted that when calculating slopes of segments these should be defined by the coordinates of intersection even if these are only estimated, rather than estimates of the slopes themselves, ie:

$$m_3 = \frac{Y_4 - Y_3}{X_4 - X_3}$$

This prevents the occurrence of disruption of the models at the intersection of the segments.

For the purposes of input data to the program the segments have been defined in terms of the lower value of X at which the segment becomes effective, the slop directed towards increasing X, and the value of Y appropriate to the lower value of X.

In the case of both lamp and fog models the initial value of X will be zero, whilst for lamps the value of both the slope and Y for the final segment will normally be zero. Failure to observe this practice in cases of normal light distributions which fall off with angle from the principal axis may give rise to the anamolous condition of negative intensity. Similarly in defining vertical fog density which decreases with height care must be taken to prevent the occurrence of negative for (clearer than clear!).

During a recent study of visual sequences it was found that the lamps were adequately described by five segments, however the facility for a variable number of segments has been retained for both fog and pilot's eye path models.

APPENDIX B

The various models and program controls are read in the following order:
ENTRY POINTS  1. LAMPS (light distribution)
              2. LIGHTING PATTERN (configuration)
              3. ET (visual threshold)
              4. FOG (vertical model)
              5. PILOT (eye path)
              6. CASE (output and program control).

The form of the data required to establish the above models is set out below:
(ENTRY POINT 1)
LAMPS (refer Appendix A)
NL number of different lamp models to be read
(the first model read is subsequently known as lamp 1)
$R_1$ ratio of AZ/EL axes in isocandle diagram.
(First lamp)

$\theta_1 = 0.0$  $M_1$  $I_1$ ⎫ $\theta$ is the angle at the break
$\theta_2$       $M_2$  $I_2$ ⎪ point in degrees
$\theta_3$       $M_3$  $I_3$ ⎬ M is the slope of the segment
$\theta_4$       $M_4$  $I_4$ ⎪ in candela/degree
$\theta_5$       $M_5 = 0.0$  $I_5 = 0.0$ ⎭ I is the intensity at the break point in candela NB: five elements describing one half of the vertical light distribution.
(NL th lamp)
$R_{NL}$ $\theta_{1NL} = 0.0$  $M_{1NL}$  $I_{1NL}$
$\theta_{2NL}$       $M_{2NL}$  $I_{2NL}$
$\theta_{3NL}$       $M_{3NL}$  $I_{3NL}$
$\theta_{4NL}$       $M_{4NL}$  $I_{4NL}$
$\theta_{5NL}$       $M_{5NL}$  $I_{5NL} = 0.0$ (ENTRY POINT 2)
LIGHTING PATTERN
LP Lateral position of line of lights
NT Total number of blocks of all lamp types.              $\geq 1$
NE Total number of blocks of all lamp elevation settings. $\geq 1$
NA Total number of blocks of all lamp azimuth settings.   $\geq 1$
NI Total number of blocks of all lamp intensity factors.  $\geq 1$
The following positions are those of the downwind end of blocks.

| | |
|---|---|
| $POT_1$ | $LT_{NT}$ |
| position of block 1 for lamp type | lamp type in block 1 |
| position of block 1 for lamp type | lamp type in block 1 |
| position of block 1 for lamp type | lamp type in block 1 |
| $POT_{NT}$ | $LT_{NT}$ |
| position of block NT for lamp type | lamp type in block NT |
| $POE_1$ | $LE_1$ |
| position of block 1 for elevation | lamp elevation in block 1 |
| position of block 1 for elevation | lamp elevation in block 1 |
| position of block 1 for elevation | lamp elevation in block 1 |
| $POE_{NE}$ | $LE_{NE}$ |
| position of block NE for elevation | lamp elevation in block NE |
| $POA_1$ | $LA_1$ |
| position of block 1 for azimuth | lamp azimuth in block 1 |
| position of block 1 for azimuth | lamp azimuth in block 1 |
| position of block 1 for azimuth | lamp azimuth in block 1 |
| $POA_{NA}$ | $LA_{NA}$ |
| position of block NA for azimuth | lamp azimuth in block NA |
| $POI_1$ | $LI_1$ |
| position of block 1 for intensity factor | 1 lamp intensity factor in block 1 |
| position of block 1 for intensity factor | 1 lamp intensity factor in block 1 |
| position of block 1 for intensity factor | 1 lamp intensity factor in block 1 |
| $POI_{NI}$ | $LI_{NI}$ |

-continued
APPENDIX B position of block NI for intensity factor
lamp intensity factor in block NI
$R_P$ upwind end of last block in the line of lights.

(ENTRY POINT 4)
FOG
MODEL NUMBER specifying type of model in use may assume values of 1, 2 or 3.
1 Continuous statistical model of mean extinction coefficient.
2 Segmented function of mean extinction coefficient.
3 Segmented function of extinction coefficient.
HN number of elements in segmented fog models 2.
Note: No illustration of the use of segmented fog models is given, if such models are required the technique described in Appendix A should be followed.
For the continuous model, HN should assume a dummy value of 1. The vertical profile is specified by two parameters $S_G$ and C, where $S_G$ is the extinction coefficient (km$^{-1}$) at a height of 2 m and C is a constant related to the probability of occurrence. This is used to obtain the mean extinction coefficient $\bar{S}$ by means of an equation within the program as set out below.

$$\bar{S} = [(S_G + (C \times 0.0001 (H - 2)S_G)^{\frac{1}{2}})(H - 2) + S_G \times 2]/H$$

where the height H is given in meters.
(ENTRY POINT 5)
PILOT
    NH number of elements in height position model    $\geq 2$
    NL number of elements in lateral position model    $\geq 2$

| | | | |
|---|---|---|---|
| $X_1$ | $S_1$ | $Z_1$ | |
| $X_1$ | $S_1$ | $Z_1$ | X or XX is range at the break point in meters |
| $X_1$ | $S_1$ | $Z_1$ | |
| $X_{NH}$ | $S_{NH}$ | $Z_{NH}$ | S or SS is slope of segment in meters/meter |
| $XX_1$ | $SS_1$ | $Y_1$ | |
| $XX_1$ | $SS_1$ | $Y_1$ | Z and Y are the height and lateral displacement at the break point in meters. |
| $XX_1$ | $SS_1$ | $Y_1$ | |
| $XX_{NL}$ | $SS_{NL}$ | $Y_{NL}$ | |

$U_W$   $D_W$   upwind and downwind limits of the pilot's eye path.
Note: The upwind limit should be downwind of both the extreme values (ie $X_{NH}$ and $XX_{NL}$) of the eye path models.
(ENTRY POINT 6)
CASE
HTU a three digit number controlling the form of the output.
  Hundreds  Program mode control
                  0 far point computed
                  1 near point computed
  Tens  Tabulation output control
                    $\geq 1$ basic parameter tabulation on line printer
                    $\geq 2$ additional program progress and state indicators
  Units  Digital plotter control
                    <5 generate new axes for plotter
                    >5 superimpose next plot on existing axes
                    0 plotter output suppressed
                    1 or 6 height/visual ground range
                    2 or 7 height/elevation offset angle
                    3 or 8 height/azimuth offset angle
                    4 or 9 (not allocated)
RUN a serial or date number up to 6 digits (appears on all tabulations and plots).
INSTRING caption for all tabulations (and plots when new axes are generated), up to 120 characters within apostrophies.
NC number dictating entry point for subsequent case.
1 LAMPS
2 LIGHTING
3 ET    (entry at a given point requires that and
4 FOG    all following models to be re-read).
5 PILOT
6 CASE
N number exceeding 6 terminates program.

In the above, code letters have been used to represent variables. These have been chosen to act as shorthand descriptions of the variables and users assembling input data may find their use as annotations eases the task of maintaining the correct data format.

APPENDIX C

LAMPS
  2
  2.0
  0.0        −1000.0      7500.0
  0.5        −2333.3      7000.0
  2.6        −615.4       2100.0
  5.2        −100.0       500.0
  10.2       0.0         0.0
  2.4
  0.0        −1666.7     30000.0
  0.6        −5239.4     29000.0
  4.15      −3125.0     10400.0
  6.55      −1054.5     2900.0
  9.3        0.0         0.0
LIGHTING PATTERN
  0.0
  2
  5
  1
  2
  900.0      2
  0.0        1
  900.0      6.0
  650.0      5.5
  450.0      5.0
  300.0      4.5
  0.0        3.0
  900.0      0.0
  900.0      1.0
  0.0        0.33
 −1500.0
ET
  −4.0
FOG
  1
  1
  8.76       1.50
PILOT
  6
  2
  −1100.0     0.0         8.9
  −605.0      0.01808    8.9
  −345.0      0.02263    13.6
  −155.0      0.03053    17.9
  −60.0       0.04188    20.8
  +100.0      0.05241    27.5
 −1500.0     0.0         0.0
  0.0         0.0         0.0
LIMITS
  −620.0      +300.0
CASE
  0.21
  100574
  'B747 3 DEG AUTOLAND ICAO LIGHTING DAY P OF FOG GRADIENT
  = 0.5 5/6/7*10 2 M RVR'
  6
  106
  2
  'NEAR PT'
  4
FOG
  1
  1
  6.69       1.50
PILOT
  6
  2
  −1100.0     0.0         8.9
  −605.0      0.01808    8.9
  −345.0      0.02263    13.9
  −155.0      0.03053    17.9
  −60.0       0.04188    20.8
  +100.0      0.05241    27.5
 −1500.0     0.0         0.0
  0.0         0.0         0.0
LIMITS
  −620.0      +400.0
CASE
  006
  3

```
-continued
      'FAR PT'
         6
        106
         4
      'NEAR PT'
(The remainder has been omitted for brevity)
         7
              APPENDIX D
RUN IDENT 100574 B747 3 DEG AUTOLAND ICAO
LIGHTING DAY P OF FOG GRADIENT
= 0.5 5/6/7*10 2 M RVR
LAMP  1 AZIMUTH FACTOR 2.00
       Angle      Slope       Intensity
       0.00      -1000.0      7500.0
       0.50      -2333.3      7000.0
       2.60      -615.4       2100.0
       5.20      -100.0       500.0
       10.20      0.0         0.0
LAMP  2 AZIMUTH FACTOR 2.40
       Angle      Slope       Intensity
       0.00      -1666.7      30000.0
       0.60      -5239.4      29000.0
       4.15      -3125.0      10400.0
       6.55      -1054.5      2900.0
       9.30       0.0         0.0
LATERAL POSITION 0.0
LIGHTING PATTERN
       Position   Angle       Type
       900.0                   2
       0.0                     1
ELEVATION
       900.0      6.00
       650.0      5.50
       450.0      5.00
       300.0      4.50
       0.0        3.00
AZIMUTH
       900.0      0.00
INTENSITY FACTOR
       900.0      1.00
       0.0        0.33
RUNWAY STOP END  -1500.0
LUMINANCE THRESHOLD  -4.00
FOG EXTINCTION COEFFICIENT
       Height     Slope       Sigma
                              8.76      1.50
PILOT EYE PATH
   A/C  Position  Slope       Height
        -1100.0   0.0000      8.9
        -605.0    0.0181      8.9
        -345.0    0.0226      13.6
        -155.0    0.0305      17.9
        -60.0     0.0419      20.8
        100.0     0.0524      27.5
   A/C  Position  Slope       Lateral
        -1500.0   0.0000      0.0
        0.0       0.0000      0.0
Computation Limits Upwind  -620  Downwind 300
Output Option 21
```

In shallow fog conditions a tall aircraft override facility 41 gives information as to the minimum height a pilot must be from the ground when the aircraft is landed for uninterrupted visual acquisition of runway lighting.

FIGS. 4 and 5 illustrate the variation of slant extinction coefficient with height in actual shallow and deep fog situations together with model profiles fitted to accord with the three transmissometer measurements. As shown in FIGS. 4a and 5a, the model and the empirical profiles deviate one from another by no more than ±5%, a correlation which has been found consistent throughout all deep and shallow fog conditions examined by the inventor and which conditions are by far the more common in any fog timescale. Thus is validated his discovery that a reliable estimate can be obtained from just three slant readings at different heights.

I claim:

1. An apparatus for estimating slant visual range in fog comprising:

a transmissometer array, having at least three transmissometer elements at respectively greater differing heights $h_1$, $h_2$ and $h_3$ above the ground and disposed for operation between the differing heights and ground level, for generating transmissometer signals indicative of a fog strength; and a slant visual range (SVR) computer coupled to said transmissometer array so as to receive the transmissometer signals therefrom, said SVR computer having:

means for converting the transmissometer signals into signals $\bar{\sigma}h_1$, $\bar{\sigma}h_2$, $\bar{\sigma}h_3$ representing the mean integral of extinction coefficient between said respectively greater heights $h_1$, $h_2$, $h_3$, above ground and ground level;

means for storing a predetermined set of extinction coefficient $\bar{\sigma}_h$ function models, each model characterising a different type of fog pattern, each model having predetermined criteria for its selection and use, and containing at least one empirical constant;

means for selecting one of the models in accordance with values of $\bar{\sigma}h_1$, $\bar{\sigma}h_2$, $\bar{\sigma}h_3$ determined by said converting means;

means for determining the values of the empirical constant in the selected model thus obtaining a definitive extinction coefficient profile, means for storing values representing airfield lighting and accepting values representing flight path and background brightness, and means for estimating slant visual range from the definitive profile and the airfield lighting, background brightness and flight path values.

2. An apparatus according to claim 1 and wherein said converting means comprises means for converting the transmissometer array signals into $\bar{\sigma}_h$ signals in accordance with the function:

$$\bar{\sigma}_h = \frac{1}{-R} \mathrm{Log}_e \frac{I_h}{I_o}$$

where

R is the distance over which the measurement is taken;

$I_h$ is the signal from said transmissometer array, and $I_o$ is a clear day datum transmissometer signal.

3. An apparatus according to claim 1 wherein the means for storing function models comprises means for storing the following predetermined set of models and their respective predetermined criteria for selection and use:

Model #1: $\bar{\sigma} = ah^2 + bh + c$ for use when $\bar{\sigma}_{h3} > \bar{\sigma}_{h2} > \bar{\sigma}_{h1}$ Model #2: $\bar{\sigma}_{hu} = \frac{p}{qh_3 + r}$ and $\bar{\sigma}_{hL} = j(h_2 \text{ or } h_1) +$ $k$ for use when $\bar{\sigma}_{h3} < \bar{\sigma}_{h2} > \bar{\sigma}_{h1}$, Model #3: $\bar{\sigma}_{hu} = \frac{p}{q(h_3 \text{ or } h_2) + r}$ and $\bar{\sigma}_{hL} =$ $k$ for use when $\bar{\sigma}_{h3} < \bar{\sigma}_{h2} < \bar{\sigma}_{h1}$ where a, b, c, j, k, p, q, r are empirical constants and $\bar{\sigma}_{hU}$ and $\bar{\sigma}_{hL}$ are mean integrals of extinction coefficient between the ground and a height above and below the fog top respectively.

4. An apparatus according to claim 1 further including means for determining a visual sequence from the selected $\overline{\sigma}_h$ function model.

5. An apparatus according to claim 1 wherein said deriving means includes means for determining the intersection of the function:

$$\text{Visual contact height } (H_c) = \frac{\gamma(\text{Log}_{10}E_T)\alpha}{\overline{\sigma}h_c}$$

with the definitive model, where $\gamma$ and $\alpha$ are empirical constant respectively related to a flight path about and lighting pattern characteristics of an airport;

$E_T$ represents an eye illuminance threshold, measured in lux, and $\overline{\sigma}h_c$ is the mean integral of the extinction coefficient profile at the visual contact height.

6. An apparatus according to claim 5 further comprising means for deriving the value $\text{Log}_{10}(E_T)$ for use in the $H_c$ function when the value of $E_T$ is not known, from the function:

$$\text{Log}_{10}(E_T) = u \log_{10}\beta - v,$$

where $\beta$ represents background brightness in nits and u and v are empirical constants.

7. An apparatus according to claim 1 further comprising a brightness measuring detector mounted on the transmissometer array for deriving the value of $\beta$.

8. An apparatus according to claim 6 and further comprising means for comparing the value of $\text{Log}_{10}(E_T)$ with a value $-w$ and for limiting the value of $\text{Log}_{10}(E_T) \geq -w$, where w is an accustomation factor for night use, the limited value being used in the $H_c$ function.

9. Apparatus according to claim 5 further comprising:
means for storing aircraft configuration data;
means for applying the aircraft configuration data to the derived $H_c$ value; and
means for modifying the $H_c$ function in accordance with the aircraft configuration data.

10. Apparatus according to claim 4 wherein the SVR computer comprises iteratively operable means for applying to the selected model, the particular lighting patterns, direction, intensity and visual threshold values at a sequence of aircraft positions, during a landing run.

11. An apparatus according to claim 1 wherein said transmissometer elements disposed for operation at three different heights above the ground comprise reflector elements.

12. An apparatus according to claim 1 wherein said transmissometer array comprises a source/detector transmissometer unit mounted substantially at ground level and a plurality of reflector elements mounted at different heights.

13. An apparatus according to claim 1 wherein $h_3$ is substantially 30 meters.

14. An apparatus according to claim 1 wherein said transmissometer array is mounted on a tower disposed at least 370 meters laterally from the center line of a runway.

15. An apparatus according to claim 1 wherein said transmissometer array is mounted on a tower disposed at least 350 meters ahead of a runway threshold.

16. An apparatus according to claim 1 further including a distinct transmissometer separate from said transmissometer array and for substantially horizontal operation up to 4 meters above ground to provide a confirmation of the fog extent and of the $\overline{\sigma}_h$ profile estimate.

17. An apparatus for estimating slant visual range in fog, comprising:

a transmissometer array disposed for slant operation and having reflector elements disposed at respectively greater different heights $h_1$, $h_2$ and $h_3$ above ground and a source/detector unit transmissometer unit mounted substantially at ground level, said array being arranged for generating signals indicative of a fog structure;

a background brightness detector, and signal processing means, arranged for receiving said signals derived from said transmissometer array and signals representing background brightness from said brightness detector and for estimating slant visual range, said signal processing means comprising:

converter means for converting the transmissometer signals into signals $\overline{\sigma}h_1$, $\overline{\sigma}h_2$, $\sigma h_3$ representing the mean integral of extinction coefficient between the respectively greater heights $h_1$, $h_2$, $h_3$, (and the ground, said converter means for converting) in accordance with the function $$\overline{\sigma}h = \frac{1}{-R}\text{Log}_e\frac{I_h}{I_o}$$

where

R is the distance over which the measurement is taken, $I_h$ is the fog structure indicative signal from the transmissometer in respect of a height $h_1$, $h_2$, $h_3$, and $I_o$ is a clear day datum transmissometer signal, comparison means for comparing the $\overline{\sigma}h$ signals and selecting one model from the following groups of three (3) models in accordance with the predetermined criteria associated with each model Model 1: $\overline{\sigma}h = ah^2 + bh + c$ for use when $\overline{\sigma}h_3 > \overline{\sigma}h_2 > \overline{\sigma}h_1$ Model 2: $\overline{\sigma}h_U = \frac{p}{qh_3 + r}$ and $\overline{\sigma}h_L = j(h_2 \text{ or } h_1) +$ k for use when $\overline{\sigma}h_3 < \overline{\sigma}h_2 > \overline{\sigma}h_1$, Model 3: $\overline{\sigma}h_U = \frac{p}{q(h_3 \text{ or } h_2) + r}$ and $\overline{\sigma}h_L =$ k for use when $\overline{\sigma}h_3 < \overline{\sigma}h_2 < \overline{\sigma}h_1$ where a, b, c, j, k, p, q, r are empirical constants and $\overline{\sigma}h_U$ and $\overline{\sigma}h_L$ are mean integrals of extinction coefficient between the ground and a height above and below the fog top respectively, determining means, coupled to said comparison means, for determining the values of the empirical constants in the selected model to establish a definitive model, store means for storing values representing airfield lighting and accepting values representing flight path, $Log_{10}(E_T)$ deriving means operative to determine the value of $Log_{10}(E_T)$ from the function $$Log_{10}(E_T) = u\ log_{10}\ \beta - v$$

where $E_T$ represents the eye illuminance threshold, measured in lux, $\beta$ represents background brightness in nits and u and v are empirical constants; (and)

Visual contact height determining means coupled to said $Log_{10}(E_T)$ determining means, for determining the intersection of the function $$\text{Visual Contact Height } (H_C) = \frac{\gamma(Log_{10}E_T)\alpha}{\sigma h_c}$$

with the definitive model,
where $\gamma$ and $\alpha$ are empirical constants respectively related to flight path about the lighting pattern of an airport, and iterative visual sequence determination means coupled to said comparison means and to said store means for providing a visual sequence.

* * * * *